United States Patent
Colli

(10) Patent No.: US 12,409,142 B2
(45) Date of Patent: *Sep. 9, 2025

(54) MODIFIED RELEASE ORAL CONTRACEPTIVE COMPOSITION

(71) Applicant: CHEMO RESEARCH, S.L., Madrid (ES)

(72) Inventor: Enrico Colli, Madrid (ES)

(73) Assignee: CHEMO RESEARCH, S.L., Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 18/660,021

(22) Filed: May 9, 2024

(65) Prior Publication Data

US 2024/0350415 A1    Oct. 24, 2024

Related U.S. Application Data

(63) Continuation of application No. 18/021,165, filed as application No. PCT/EP2021/072584 on Aug. 13, 2021.

(30) Foreign Application Priority Data

Aug. 14, 2020 (EP) ..................................... 20382753

(51) Int. Cl.
| | | |
|---|---|---|
| *A61K 9/20* | (2006.01) | |
| *A61K 31/567* | (2006.01) | |
| *A61K 47/26* | (2006.01) | |
| *A61K 47/32* | (2006.01) | |
| *A61P 15/18* | (2006.01) | |

(52) U.S. Cl.
CPC .......... *A61K 9/2054* (2013.01); *A61K 31/567* (2013.01); *A61K 47/26* (2013.01); *A61K 47/32* (2013.01); *A61P 15/18* (2018.01)

(58) Field of Classification Search
CPC .... A61K 9/2054; A61K 31/567; A61K 47/26; A61K 47/32; A61P 15/18
See application file for complete search history.

(56) References Cited

FOREIGN PATENT DOCUMENTS

| CA | 2594939 A1 | 8/2006 | |
|---|---|---|---|
| CN | 101123952 A | 2/2008 | |
| WO | 9426207 A1 | 11/1994 | |
| WO | 2004110408 A2 | 12/2004 | |
| WO | WO-2006087177 A2 * | 8/2006 | ........... A61K 31/565 |
| WO | 2010/015713 A1 | 2/2010 | |

OTHER PUBLICATIONS

Gerstman, "Oral contraceptive estrogen dose and the risk of deep venous thromboembolic disease," *American Journal of Epidemiology* 134(9):1009-1010, Jan. 1991. (2 pages).

Guida et al., "Review of the safety, efficacy and patient acceptability of the combined dienogest/estradiol valerate contraceptive pill," *International Journal of Women's Health* 2010:2:279-290, Aug. 2010. (12 pages).

Helmerhorst et al., "Venous thromboembolism and the pill. The WHO technical report on cardiovascular disease and steroid hormone contraception: state-of-the-art," *Human Reproduction* 13(11):2981-2983, Nov. 1998. (3 pages).

Hoogland et al., "Ultrasound Evaluation of Ovarian Activity Under Oral Contraceptives," *Contraception* 47:583-590, Jun. 1993. (8 pages).

Landgren et al., "Hormonal profile of the cycle in 68 normally menstruating women," *Acta Endocrinologica* 94:89-98, May 1980. (10 pages).

Lidegaard, "Oral contraception and risk of a cerebral thromboembolic attack: results of a case-control study," *BMJ* 306:956-963, Apr. 1993. (8 pages).

Klipping et al., "Ovulation-Inhibiting Effects of Dienogest in a Randomized, Dose-Controlled Pharmacodynamic Trial of Healthy Women," *Journal of Clinical Pharmacology* 52:1704-1713, Nov. 2012. (10 pages).

Meade, "Oral contraceptives, clotting factors, and thrombosis," *American Journal of Obstetrics& Gynecology* 142(6, Part 2):758-761, Mar. 1982. (4 pages).

Nappi et al., "Real-world experience of women using extended-cycle vs monthly-cycle combined oral contraception in the United States: the National health and Wellness Survey," *BMC Women's Health* 18:22, Jan. 2018. (8 pages).

Stanczyk et al., "Ethinyl estradiol and 17β-estradiol in combined oral contraceptives: pharmacokinetics, pharmacodynamics and risk assessment," *Contraception* 87:706-727, Jun. 2013. (22 pages).

Vasconcelos et al., "Solid dispersions as strategy to improve oral bioavailability of poor water soluble drugs," *Drug Discovery Today* 12(23/24):1068-1075, Dec. 2007. (8 pages).

Wiegratz et al., "Effect of four different oral contraceptives on various sex hormones and serum-binding globulins," *Contraception* 67:25-32, Jan. 2003. (8 pages).

Wiegratz et al., "Effect of four oral contraceptives on hemostatic parameters," *Contraception* 70:97-106, Aug. 2004. (10 pages).

Wiegratz et al., "Effect of extended-cycle regimen with an oral contraceptive containing 30 mcg ethinylestradiol and 2 mg dienogest on bleeding patterns, safety, acceptance and contraceptive efficacy," *Contraception* 84:133-143, Aug. 2011. (11 pages).

Gerstman et al., "Oral Contraceptive Estrogen Dose and the Risk of Deep Venous Thromboembolic Disease," *American Journal of Epidemiology* 133(1):33-37, 1991. (6 pages).

(Continued)

*Primary Examiner* — Jessica Worsham
(74) *Attorney, Agent, or Firm* — Seed Intellectual Property Law Group LLP

(57) ABSTRACT

The invention relates to a new modified release oral pharmaceutical form comprising 17α-cyanomethyl-17-ß-hydroxyestra-4,9-dien-3-one (dienogest) and 17α-ethinylestradiol (ethynyl estradiol), its method of production and its medical and non-medical uses, in particular its use in contraception.

24 Claims, 8 Drawing Sheets

(56) References Cited

OTHER PUBLICATIONS

Biskupska-Bodova et al., "A randomised double-blind trial to determine the bleeding profile of the prolonged-release contraceptive dienogest 2 mg/ethinylestradiol 0.02 mg versus an immediate-release formulation of drospirenone 3 mg/ethinylestradiol 0.02 mg," The European Journal of Contraception & Reproductive Health Care 30(1):3-12, 2025. (11 pages).

* cited by examiner

MODIFIED RELEASE ORAL CONTRACEPTIVE COMPOSITION

FIELD OF THE INVENTION

The present invention pertains to the field of women's health and more specifically contraception. In particular, it relates to a new modified release oral pharmaceutical form comprising 17α-cyanomethyl-17-ß-hydroxyestra-4,9-dien-3-one (dienogest) and 17α-ethinylestradiol (ethynyl estradiol), its method of production and its medical and non-medical uses, in particular its use in contraception.

BACKGROUND OF THE INVENTION

Combined oral contraceptives (COCs) are among the most common methods of reversible birth control. Although effective in preventing pregnancy, these combinations have shown some safety and tolerability issues.

It is known that some women experience adverse events while taking oral contraceptives, including breast tenderness, headache, nausea, mood swings and loss of libido. In addition, epidemiological studies have shown a dose dependent increased risk of arterial and venous thrombotic events (VTEs). Presence of adverse events, as well as irregular bleeding patterns are often leading to lack of compliance and discontinuation, exposing women to a higher risk of pregnancy. The use of low-dose oral contraceptives containing ≤35 mcg EE has been reported to decrease incidence of VTEs and other adverse events of COCs (Helmerhorst F M, 1998; Meade T W. 1982; Gerstman B B et al., 1991; Lidegaard O. 1993; Guida et al. 2010; Stanczyk et al. 2013). Accordingly, there has been a sustained effort to reduce the dose of EE in COCs.

The synthetic progestogen dienogest (DNG) is known to have a protective effect on the endometrium, to be well tolerated and associated with high contraceptive efficacy when combined with the synthetic estrogen ethinyl estradiol (EE). The COC Valette™ (Bayer Schering Pharma AG, Germany), containing 2 mg DNG and 0.03 mg EE, is a low dose DNG/EE oral contraceptive marketed with a regimen of 21 days active pill intake followed by 7 tablet-free days. This COC has also been studied in an extended regimen of 84 days of pill intake followed by 7 tablet-free days. The extended-cycle use was reported to be effective and mostly well tolerated, appearing to be a favorable option for women who don't wish to bleed every month (Wiegratz et al. 2011).

Wiegratz et al. 2003 evaluated the effect of decreasing the EE dose of a DNG/EE contraceptive combination to 20 mcg EE or below. In particular, they compared the contraceptive activity and cycle control of 30 mcg EE/2 mg DNG with oral dosage forms comprising 20 mcg EE+2 mg DNG (20EE/DNG), 10 mcg EE+2 mg estradiol valerate (EV)+2 mg DNG (EE/EV/DNG) or 20 mcg EE+100 mcg levonorgestrel (LNG) (EE/LNG). The tablets were taken for six cycles (21 days and 7 days of hormone-free interval). In this study, the cycle control was significantly better with 30EE/DNG or EE/LNG than with 20EE/DNG or EE/EV/DNG. Thus, the reduction of the EE dose to 20 mcg or lower had to be compensated by more potent progestins, in order to maintain an appropriate cycle control.

This is in line with the findings of Stanczyk et al. 2013, showing that while lowering the dose of EE from 35 to 20 mcg resulted in reduced symptoms of breast tenderness, nausea and dizziness, it was found to be associated with a higher incidence of unscheduled bleeding than in COCs with a higher EE dose.

CA 02594939 (WO 2006/087177) relates to an oral pharmaceutical form comprising DNG equal to or less than 2.0 mg and EE less than 0.030 mg, where DNG is released proportionately in two phases and one of the phases is released with a time delay relative to the other phase. More specifically, DNG has a rapid (non-slow) in vitro release within the first phase and a delayed (slow) in vitro release within the second phase; EE has a conventional rapid in vitro release. This document does neither provide any experimental data showing the efficacy of the disclosed compositions in the inhibition of ovulation nor information on its bleeding pattern.

Besides, Guida et al. 2010 evaluated an oral contraceptive with a four-phasic dose regimen wherein the progestogen is DNG and EE is replaced by natural 17β-estradiol (E2), in the form of estradiol valerate (EV). This oral contraceptive includes four hormonal dosage steps in which estrogen and progestin doses follow as close as possible the menstrual cycle physiology. In particular, E2V is combined with DNG in a four-phasic dose regimen wherein the first two tablets contain 3 mg E2V; the next five tablets include 2 mg E2V+2 mg DNG, followed by 17 tablets with 2 mg E2V+3 mg DNG; followed by two tablets with 1 mg E2V only, and finally two placebo tablets. Previous attempts to replace EE with E2, particularly when E2 was administered as part of a monophasic or a biphasic treatment resulted in an unacceptable bleeding pattern. The solution provided by Guida et al. 2010 results in a significant increase in the total amount of DNG in comparison to one cycle administration (21+7 hormone-free) administration of Valette™ (61 mg vs 42 mg).

Despite significant progresses, it is still desirable to develop new DNG/EE oral contraceptive forms containing low dosages of EE, such as 0.02 mg of EE or less, which are well tolerated, provide a reliable contraceptive efficacy and an acceptable bleeding pattern.

SUMMARY OF THE INVENTION

The present invention relates to a prolonged-release DNG and EE oral contraceptive composition comprising 2 mg of DNG and equal to or less than 0.02 mg of EE, preferably 2 mg of DNG and 0.02 mg of EE.

The prolonged release formulation of the invention has been shown by the inventors in Phase II clinical trials to be well tolerated (comparable to the immediate release reference product Valette™) and provide a reliable contraceptive efficacy with an adequate bleeding pattern. The prolonged release formulations of the invention presented a better profile than the reference product Velmari®.

In Example 1 it was shown that all tested DNG and EE prolonged-release formulations (i.e. T1: 2 mg DNG+0.02 mg EE; T2: 1 mg DNG+0.01 mg EE; T3: 2 mg DNG+0.01 mg EE) were safe and well tolerated after multiple dose of once daily administration for 7 days in healthy premenopausal females. The tolerability of the three investigational prolonged release (PR) formulations was comparable to the immediate release reference product Valette™ (2 mg DNG+0.03 mg EE).

After repeated daily intake over 7 days of administration, the main pharmacokinetic characteristics of the three Test PR were:

Tmax shifted from 1.5 hours to approximately 4 hours in the PR formulations.

AUC0-24 h was strictly proportional compared to the immediate release reference product.

Peak Through Fluctuations were reduced in the PR formulations compared to immediate release reference product (Cmax was reduced by approx. 25% and Cmin was slightly higher in the PR formulations).

The Phase II study described in Example 2 was performed to assess the inhibition of ovarian activity of the prolonged release DNG and EE formulation described herein, explore its further effects on reproductive parameters and assess the safety and tolerability of three different strengths. The three strengths tested were T1 (EE/DNG 10 µg/1 mg), T2 (10 µg/2 mg), and T3 (20 µg/2 mg). The extended-regimen Velmari® (EE 20 µg/drospirenone 3 mg) was used as a reference product since in the tested drugs the maximum content of EE is of 0.02 mg (which is lower than the 0.03 mg in Valette™).

In this Ph II clinical trial the selected dosage regimen was an extended regimen wherein the oral contraceptives were administered for 4 consecutive cycles (TC1 to TC4), wherein TC1 to TC3 corresponds to a first treatment period (extended) 87 days intake+4 hormone-free days (91); and TC 4 to a second treatment period of 24 days intake+4 hormone-free days.

The PR composition at EE 20 µg/DNG 2 mg inhibited the ovarian activity most effectively. It induced 100% inhibition of ovulation, and with no or minimum ovarian activity in the largest number of subjects (using the Hoogland score). The results were highly similar to the reference product Velmari®. The ovarian suppression was confirmed by the TVU findings and hormone levels.

The bleeding pattern was least favorable in the Velmari® group with a mean value of only 76 bleeding-free days, compared with 78 days for T3 (20 µg/2 mg), 87 days for T2 (10 µg/2 mg), and 89 days for T1 (EE/DNG 10 µg/1 mg), TC 1 to TC 4 inclusive.

Also, during the TC1-TC3 period, the PR formulations of the invention presented a more favorable profile with respect to the number of "heavy" bleeding, as well as for "spotting" and "no bleeding" days.

All products were safe and well tolerated. One single serious AE reported in this study was unrelated to the investigational medicinal product (IMP) and occurred under Velmari® treatment. The safety data did not reveal any clinically meaningful differences between the treatment groups.

Accordingly, the first aspect of the invention relates to an oral composition (preferably, an oral contraceptive composition) comprising 2 mg of DNG and equal to or less than 0.02 mg of EE, wherein the pharmaceutical form of said composition is a modified release form, wherein at least 80%, preferably at least 85%, at least 90%, at least 95%, at least 97%, at least 99%, and more preferably all the content of EE is intended for slow release.

In a second aspect, the present invention relates to a process for the preparation of an extended release oral dosage form as described herein.

In a third aspect, the present invention relates to the use of the oral composition as described herein in contraception, in other words, it provides the oral composition as described herein as a contraceptive composition.

In a related aspect pertains to an oral contraceptive method for a female subject, preferably a premenopausal female, in need thereof characterized in that it comprises the step of administering active daily dosage units of an oral composition as described herein to said female subject over a period of several consecutive days.

In a further aspect, the present invention also provides an oral composition as described herein for use in the treatment of one or more of acne, endometriosis, dysmenorrhea, dysfunctional uterine bleeding, cycle dependent complains or uterine fibroids in a female subject.

In a related aspect, it refers to a method of treating one or more of the diseases or disorders mentioned above, wherein said method comprises administering to a female subject, preferably a premenopausal female, in need thereof, a therapeutically effective dosage of an oral composition as described herein.

In a further related aspect, the present invention provides the use of an oral composition as described herein for the manufacturing of a medicament for the treatment of one or more of the diseases or disorders mentioned above.

In an additional aspect, the present invention also provides a kit based on the compositions described herein. Such a kit is particularly suitable for use in the contraceptive and medical methods as described herein.

DETAILED DESCRIPTION OF THE INVENTION

Definitions

Figure 1:
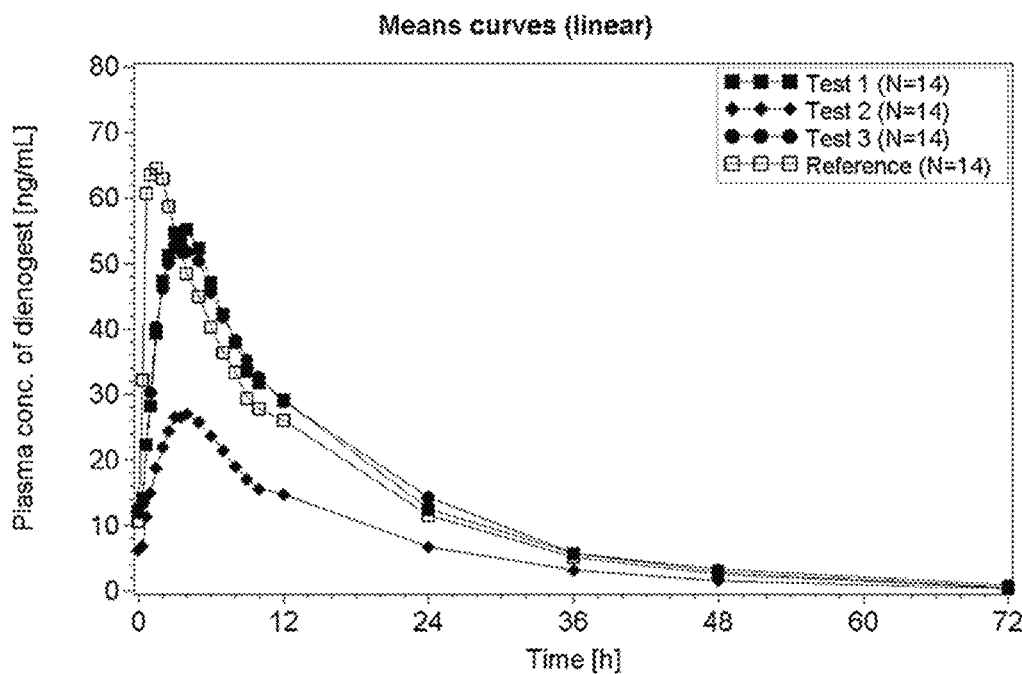
FIG. 1. Mean (arithmetic) dienogest plasma concentration-time profile (linear) after oral administration of a multiple dose once daily for 7 days.

As used herein, the term "dienogest (DNG)" or "17α-cyanomethyl-17-ß-hydroxyestra-4,9-dien-3-one" is defined for purposes of the invention as comprising (i) unsalified dienogest (also known as dienogest base), its pharmaceutically acceptable salts and mixtures thereof; as well as (ii) esters, solvates, complexes, polymorphs, hydrates or prodrugs of (i) as used herein. Preferably, the dienogest in the composition is unsalified dienogest, a pharmaceutically acceptable salt thereof, or a mixture thereof. Dienogest has PubChem CID number: 68861.

As used herein, the term "ethynyl estradiol (EE)" or "17α-ethinylestradiol" is defined for purposes of the invention as comprising (i) unsalified ethynyl estradiol (also known as ethynyl estradiol base), its pharmaceutically acceptable salts and mixtures thereof; as well as (ii) esters, solvates, complexes, polymorphs, hydrates or prodrugs of (i) as used herein. Preferably, the ethinyl estradiol in the composition is unsalified ethynyl estradiol, a pharmaceutically acceptable salt thereof, or a mixture thereof. Ethynyl estradiol has PubChem CID number: 5991.

Esters of DNG and/or EE may be prepared through functionalization of hydroxyl and/or carboxyl groups that may be present within the molecular structure of the compound (Advanced Organic Chemistry: Reactions, Mechanisms and Structure, 4th Ed. (New York: Wiley-Interscience, 1992). Pharmaceutically acceptable salts include those formed with free amino groups such as those derived from hydrochloric, phosphoric, acetic, oxalic, tartaric acids and the like, and those formed with free carboxyl groups such as those derived from sodium, potassium, ammonium, calcium, ferric hydroxides, isopropylamine, triethylamine, 2-ethyl-amino ethanol, histidine, procaine or similar.

As used herein, the mass of DNG and/or EE in any dosage form of the invention or of a test, reference, control or comparator dosage form comprising DNG and/or EE refers to the amount (mass) of unsalified DNG and/or EE, or a pharmaceutically salt of DNG and/or EE, or a mixture thereof.

As used herein with respect to the dosage form of the invention, the term "oral", "oral dosage form", "oral pharmaceutical dosage form", "oral administration", "oral compositions" "oral pharmaceutical compositions", "oral contraceptive compositions", "oral tablets", "oral capsules", "orally ingested", "orally", "oral route" and the like all refer to any method of administration through the mouth. The oral dosage form of the invention is usually ingested intact, although it may be ingested tampered (e.g., crushed) and usually with the aid of water or a beverage to hasten passage through the mouth.

As used herein, the term "extended release" dosage forms mean pharmaceutical preparations which release an active ingredient from a dosage form or a portion thereof in other than an immediate release fashion. Extended release pharmaceutical compositions are made by incorporating a controlled release material (e.g., controlled release excipients) in the dosage form. Extended release dosage forms are sometimes designed to accomplish pharmaceutical, pharmacokinetic, pharmacodynamic, therapeutic or convenience objectives not offered by conventional dosage forms such as a solution or an immediate release dosage form.

As used herein, the term "extended release" is interchangeably with "modified release", "controlled release", "prolonged release", "slow release", "sustained release", "long acting" and the like. Extended release dosage forms release the active ingredient from a dosage form or a portion thereof over an extended period of time (over a period of time of 4, 6 hours or 8 hours or greater, preferably over for period greater than about 8 hours, and most preferably over for period greater than about 10 hours, 12, 14, 16, 18, 20, 22 or 24 hours. Extended release dosage forms may be either delayed onset formulations, i.e., "delayed onset, extended release" (e.g., a delay in release of 1, 1.5, 2, 2.5, 3, 3.5, 4, 4.5, 5, 5.5, 6, 6.5, 7, 7.5 or 8 hours after ingestion, preferably at least 2 hours after ingestion) or preferably "extended release" (i.e., without a significant initial delay in release). In some embodiments, these extended release compositions are formulated to be suitable for daily administration.

As used herein, "controlled release material", "controlled release means", "rate controlling means", "rate controlling excipient", "rate controlling ingredient", "rate controlling material", "release rate controlling means", "release rate controlling excipient", "release rate controlling ingredient", "release rate controlling material", and "material to provide controlled release" means an in vitro or in vivo release rate controlling excipient or material incorporated in the dosage form whose function or primary function is to modify release (e.g., onset of release, rate of release, duration of release) of an active drug (e.g., DNG and/or EE) from a dosage form or a portion (i.e., cause the dosage form to release in other than an immediate release fashion). In more preferred embodiments of the invention, the controlled release material functions to provide one or more of the following, compared to immediate release DNG and/or EE: (1) change in the onset of release; (2) change in the rate of release; (3) change in the duration of release; (4) change in the time of peak plasma concentration; (5) change in the peak plasma concentration; (6) change in the extent of absorption; (7) change in the onset of therapeutic effect; (8) change in the duration of therapeutic effect; and (9) change in the gastrointestinal anatomic location of release.

As used herein a contraceptive method relates to a method for preventing pregnancy.

As used herein, "treatment", "treating" or "treat" refer to: (i) preventing or retarding a disease, disorder or condition from occurring in a subject which may be predisposed to the disease, disorder and/or condition but has not yet been diagnosed as having it; (ii) inhibiting the disease, disorder or condition, i.e., arresting or slowing down its development or progression; and/or (iii) relieving the disease, disorder or condition, i.e., causing regression of the disease, disorder and/or condition. In certain embodiments, such term refers to the amelioration or eradication of a disease or symptoms associated with a disease.

As used herein a "therapeutically effective amount" refers to an amount effective, at dosages and for periods of time necessary to achieve the desired therapeutic result, such as one or more of the following therapeutic results, such as a significant delay of the onset or progression of the disease; or a significant reduction of the severity of one or more symptoms.

A therapeutically effective amount is also typically one in which any toxic or detrimental effect of the active ingredient or pharmaceutical composition is outweighed by the therapeutically beneficial effects.

DETAILED DESCRIPTION

Oral Composition of the Invention

In a first aspect, the invention pertains to an oral composition (preferably, an oral contraceptive composition) comprising 2 mg of DNG and equal to or less than 0.02 mg of EE, wherein the pharmaceutical form of said composition is a modified release form, wherein at least 80%, preferably at least 85%, at least 90%, at least 95%, at least 97%, at least 99%, and more preferably all the content of EE is intended for slow or controlled release.

In preferred embodiments, at least 80%, preferably at least 85%, at least 90%, at least 95%, at least 97% or at least 99% %, and more preferably all the content of DNG and EE, wherein each is independently selected, is intended for slow or controlled release; preferably all the content of DNG and EE is intended for slow or controlled release.

In some embodiments, the dosage form of the invention is an oral dosage form (preferably a tablet) comprising: (i) 2 mg of DNG and equal to or less than 0.02 mg of EE, and (ii) controlled release material to render said dosage form suitable for extended release, preferably said dosage form suitable for dosing every 24 hours. In other words, in preferred embodiments, the composition as described herein is a daily dosage form.

Furthermore, the slow or controlled release dosage forms of the present invention may preferably release EE, preferably EE and DNG, at a rate that is independent of pH, e.g., between pH 1.6 and 7.2. In other words, the dosage forms of the present invention avoid "dose dumping" upon oral administration.

The composition of the invention comprises 2 mg of DNG and equal to or less than 0.02 mg of EE, preferably from 0.01 mg to 0.02 mg of EE, including 0.0125, 0.015, or 0.0175, more preferably 0.02 mg of EE. Said composition may contain other active ingredients. Preferably, does not contain other active ingredients with contraceptive effects. In preferred embodiments, DNG and EE are the only active ingredients in the composition.

In some embodiments, the composition of the invention is further characterized by its pharmacokinetic profile. For a given DNG and EE-containing composition, the DNG and/or EE plasma concentration versus time curve may be determined by following plasma DNG and/or EE concentration over a period of about 72 h after a single oral intake of one daily dosage unit of the said composition. Alternatively, said pharmacokinetic profile may also be obtained over a period of 7 days after a daily oral intake of said composition. The $AUC_{0h-tlast}$, the AUC(0-τ), the $C_{max}$ and the $t_{max}$ are determined based on the DNG or EE plasma concentration versus time curve.

The oral administration of said DNG and EE-containing composition is preferably performed in fasting conditions i.e. without food and not close to mealtime (i.e. in general, approximately 6 h-10 h after meal) since food ingestion may modify the absorption rate of drospirenone in the gastrointestinal tract. Generally, the study population is composed by healthy premenopausal females, including women in peri-menopause.

In some preferred embodiments, the pharmacokinetic and pharmacodynamic parameters of the specifications and claims are determined under fed conditions. In other preferred embodiments, the pharmacokinetic and pharmacodynamic parameters of the specifications and claims are determined under fast conditions. Preferably, these are determined under fast conditions.

In preferred embodiments, the $t_{max}$ and $C_{max}$ values refer to the maximum DNG or EE plasma concentration and the time to reach it, respectively, after the oral administration of a daily dosage unit of the DNG and EE-containing composition during 7 days. This $t_{max}$ and $C_{max}$ may reflect the mean $t_{max}$ and $C_{max}$, respectively, of a population under study and may be the arithmetic or geometric mean, preferably the arithmetic mean. In particularly preferred embodiments, said composition is adapted to provide a pharmacokinetic profile for EE characterized by a Tmax from 3.5 h to 4 h, preferably around 3.75 h, further to oral administration to a human premenopausal female under fasting conditions once daily for 7 days.

In some embodiments, optionally in combination with any of the above, the oral composition presents a pharmacokinetic profile further to oral administration under fasting conditions once daily for 7 days characterized by:
a. a Tmax of DNG from 3.5 h to 4 h, preferably around 3.75 h; and
b. a Tmax of EE from 3.5 h to 4 h, preferably around 3.75 h.

Preferably, the pharmacokinetic profile of said composition further to oral administration under fasting conditions once daily for 7 days is further characterized by a Cmax of EE from 60 ng/mL to 65 ng/mL. In preferred embodiments, it is further characterized by a Cmax of EE from 60 ng/mL to 65 ng/mL and a Cmax of DNG from 55 ng/mL to 60 ng/mL.

The AUC(0-t) (=$AUCt_{last}$) refers to the area under the concentration/time curve, calculated by the trapezoidal rule from time 0 h to last observed concentration at time t. The term AUC(0-τ) as used herein refers to the area under the concentration-time curve during a dosing interval. The AUC (0-τ) may reflect the mean AUC(0-τ), of a population under study and may be the arithmetic or geometric mean, preferably the arithmetic mean. In some embodiments, optionally in combination with any of the above, said composition is further characterized by having an AUC(0-τ) for EE from 680 to 710 ng*h/mL further to oral administration under fasting conditions once daily for 7 days, preferably said AUC(0-τ) is from 680 to 710 ng*h/mL and the AUC(0-τ) of DNG is from 710 to 740 ng*h/mL.

In some embodiments, optionally in combination with any of the above, the composition of the invention is further characterized by its dissolution profile. In particular embodiments, the composition as described herein is characterized by EE, preferably DNG and EE, respectively, having a dissolution profile characterized in that:
(i) no more than 25% of the amount initially present in said composition is dissolved within 1 hour; and
(ii) between 30% and 60% of the amount initially present in said composition is dissolved within 2 hours.

In preferred embodiments, at least 70%, preferably at least 80% of the amount initially present in said composition is dissolved within 8 hours. Preferably, within a range of 5 to 8 hours encompasses a time range of 5.5 to 8 hours, of 6 to 8 hours, of 6.5 to 8 hours, of 7 to 8 hours and of 7.5 to 8 hours. In particularly preferred embodiments, the composition is further characterized in that at least 70%, preferably at least 80% of the drospirenone is dissolved within 5 hours.

At least 70% of the EE and/or DNG encompasses at least 70%, at least 75%, at least 80%, at least 85%, at least 88%, at least 90%, at least 91%, at least 92%, at least 93%, at least 94%, at least 95%, at least 96%, at least 97%, at least 98%, at least 99%, at least 99.5% and 100%.

In particularly preferred embodiments, the composition as described herein is characterized by EE, preferably DNG and EE, respectively, having a dissolution profile characterized in that:
(i) no more than 25% of the amount initially present in said composition is dissolved within 1 hour;
(ii) between 35% and 55% of the amount initially present in said composition is dissolved within 2 hours, and
(iii) at least 70%, preferably at least 80% of the amount initially present in said composition is dissolved within 5 hours.

The in vitro dissolution rate of EE and/or DNG in the composition is preferably assessed by the USP1 (baskets) method. Briefly, a tablet consisting of the composition comprising EE and DNG to be tested is placed in 900 mL of water at 37° C. (±0.5° C.). The dissolution test is performed using a USP dissolution test apparatus 1 (baskets) at a stirring rate of 75 rpm.

A composition with such an in vitro dissolution profile and/or the in vivo pharmacokinetic profile described above may be achieved in different ways.

The release of the slow-release or controlled-release proportion of EE, preferably of EE and DNG, can be controlled by a large number of controlled release means. Conventional forms of retardation include coating retardation and matrix retardation. In coating retardation, the core of a pharmaceutical composition containing an active ingredient is provided with a coating which consist of one or more hydrophilic and/or hydrophobic polymers and slows down release of the active ingredient. In matrix retardation, the active ingredient is contained in a matrix which is formed from one or more excipients and controls release of the active ingredient.

Examples of these release rate controlling excipients are inert plastics matrices, hydrocolloids, ion exchangers, slow-release coatings, gastro-resistant coatings, pellet mixtures, mixtures of minitablets and/or granules, microcapsules, osmotically controlled systems, erosion-controlled systems, diffusion-controlled systems and combinations thereof, fat- and wax-containing matrices.

In some embodiments, the oral dosage form comprises a plurality of pharmaceutically acceptable beads or pellets coated with the drug and overcoated with controlled release material. These beads or pellets may be compressed into tablets or filled into hard gelatin capsules. In other embodiments, the dosage form includes a capsule within a capsule, each capsule containing a different drug or the same drug(s). In some particular embodiments, the outer capsule may be an enteric coated capsule or a capsule containing an immediate release formulation to provide rapid plasma concentrations or a rapid onset of effect or a loading dose and the inner capsule contains an extended release formulation. In one embodiment of the invention, the dosage form involves one or more tablets within a capsule, wherein the EE and/or DNG can be either in the tablet and/or in one of the capsules. In one embodiment of the invention, the composition is ingested orally as a tablet or capsule, preferably as a tablet.

In some other embodiments, the slow or controlled release behaviour is achieved by an osmotically driven release system, wherein the oral dosage form may comprise (i) a drug layer; and (ii) a displacement layer comprising an osmopolymer; and (b) a semipermeable wall surrounding the bilayer core having a passageway disposed therein for the release of the drug(s). In some embodiments, the oral dosage form comprises a compressed tablet, compressed capsule or uncompressed capsule. In some preferred embodiments, the oral dosage form comprises a tablet.

It is an object of certain embodiments of the present invention to provide oral EE and DNG, wherein the EE is dispersed within a matrix, preferably wherein EE and DNG are dispersed within a matrix. In certain preferred embodiments the oral dosage form of the present invention comprises a matrix which includes a controlled release material and EE, preferably EE and DNG. In certain preferred embodiments, the matrix is compressed into a tablet and may be optionally overcoated with a coating that in addition to the controlled release material of the matrix may control the release of the EE, preferably EE and DNG, from the formulation, such that blood levels of the active ingredient(s), are maintained within the therapeutic range over an extended period of time. In some embodiments, the coating is for immediate disintegration and release of the active ingredient. In certain alternative embodiments, the matrix is encapsulated. In some preferred embodiments, the extended release oral dosage form of the present invention comprises a plurality of pharmaceutically acceptable extended release matrices comprising EE, DNG or EE and DNG, the dosage form maintaining the blood plasma levels of the active ingredient(s) within the therapeutic range over an extended period of time when administered to patients.

In some embodiments, the dosage form of the invention comprises oral DNG and EE formulated to release the EE, preferably the EE and DNG, from the dosage form or to initiate the release of the EE, preferably the EE and DNG, from the dosage form after a certain specific amount of time post-oral ingestion, or at an approximately specific anatomic location in the gastrointestinal tract, or when the dosage form is in contact with specific gastrointestinal conditions (e.g., pH range, osmolarity, electrolyte content, food content, pressure, time since first ingestion, osmotic pressure in the dosage form, osmotic pressure in the gastrointestinal tract, hydration, etc), said dosage form suitable for providing an orally effective therapeutic for a short, intermediate or extended duration of effect, said dosage form providing a rapid or delayed onset of clinical effect. Preferably, said dosage form initiates the release of the EE, preferably the EE and DNG, immediately after ingestion.

In some embodiments of the invention, EE, preferably EE and DNG, is in the form of multiparticulates. In some embodiments of the invention, EE, preferably EE and DNG, is dispersed in a matrix. In some embodiments of the invention, EE, preferably EE and DNG, is in the form of multiparticulates that can be dispersed in a matrix or contained in a capsule. In some embodiments of the invention, EE, preferably EE and DNG, is in a matrix that is in the form of pellets. In some embodiments of the invention, EE, preferably EE and DNG is in coated beads. In some other embodiments of the invention, EE, preferably EE and DNG, is in the form of multiparticulates that are dispersed in a matrix and compressed into a tablet.

In some particularly preferred embodiments, the dosage form of the invention comprises an oral formulation (e.g., tablet or capsule) which is coated to prevent substantial direct contact of EE, preferably EE and DNG, with the oral cavity (e.g. tongue, oral mucosa), oropharyngeal mucosal surface, esophagus or stomach. In some preferred embodiments, the dosage form of the invention comprises an oral formulation which is coated with a film or polymer.

In some embodiments, optionally in combination with any of the above, said extended release form is a tablet and may be coated or not. Preferably, said tablet is a film-coated tablet comprising a tablet core and a film coating, wherein the tablet core comprises the content of EE for slow or controlled release, preferably wherein the tablet core comprises the content of DNG and EE for slow or controlled release. Preferably, the coating film allows for immediate disintegration for fast, active release. For instance, this film can be the one-step film coating system (Opadry™ II) which combines polymer, plasticizer and pigment which allows for immediate disintegration for fast, active release (Colorcon® | Opadry® II Complete Aqueous Film Coating System).

In some embodiments, the extended release EE, preferably EE and DNG, dosage form of the invention is a solid dispersion. By reducing drug particle size and therefore improving drug wettability, the bioavailability may be substantially improved. In addition, surfactants may be included to stabilize the dosage form in order to increase solubility and reduce recrystallization (see Vasconcelos et al, Drug Discovery Today, 2007; 12:1068-75, which is herein incorporated in its entirety by reference).

In some embodiments, EE (preferably EE and DNG) may be dispersed within an extended-release matrix as described herein above. The term "extended-release matrix" refers to one or more hydrophilic polymers and/or one or more hydrophobic polymers and/or one or more other type hydrophobic materials. In some embodiments, said extended release matrix comprises one or more hydrophilic polymers and one or more hydrophobic polymers, such as in hydrophobic/hydrophilic matrix systems (PVAc/PVP). Suitable materials for inclusion in an extended-release matrix (also referred herein as polymeric matrix forming agents) are:

(a) Hydrophilic polymers include but are not limited to gums, cellulose ethers, hydrophilic acrylic polymers, ammonium alginate, sodium alginate, potassium alginate, calcium alginate, propylene glycol alginate, alginic acid, polyvinyl alcohol, povidone (PVP), carbomer, potassium pectate, potassium pectinate, and protein derived materials. Of these polymers, the cellulose ethers, especially hydroxyalkylcelluloses and carboxyalkylcelluloses are preferred. The oral dosage form may contain between 10% and 80% w/w, preferably from 20% to 70%, more preferably from 30% to 60%, of at least one hydrophilic polymer.

(b) Hydrophobic polymers include but are not limited to ethyl cellulose, hydroxyethylcellulose, hydrophobic acrylic polymers and polyvinylacetate (PVAc) based polymers. Other hydrophobic materials which may be employ are digestible, long chain (C8C50, especially C12-C40), substituted or unsubstituted hydrocarbons, such as fatty acids, fatty alcohols such as cetostearyl alcohol, stearyl alcohol; cetyl alcohol myristyl alcohol etc, fatty acids, mineral and vegetable oils and waxes such as beeswax, carnauba wax, microcrystalline wax, and ozokerite. Hydrocarbons having a melting point of between 25° and 90° C. are preferred. Of these long chain hydrocarbon materials, fatty (aliphatic) alcohols are preferred. The oral dosage form may contain up to 55-60% w/w of at least one digestible, long chain hydrocarbon.

(c) Polyalkylene glycols. The oral dosage form may contain up to 60% w/w of at least one polyalkylene glycol.

In some embodiments, the dienogest: matrix forming agent weight ratio may be about 1:2.5, about 1:5, about 1:10, about 1:12.5, about 1:15, about 1:20, about 1:25, about 1:30, about 1:35, about 1:40, about 1:45 or about 1:50. In preferred embodiments, is of 1:20 to 1:30, such as about 1:20, about 1:21, about 1:22, about 1:23, about 1:24, about 1:25, about 1:26, about 1:27, about 1:28, about 1:29 or about 1:30.

The at least one hydroxyalkyl cellulose is preferably a hydroxy (C1 to C6) alkyl cellulose, preferably selected from hydroxypropylcellulose, hydroxypropylmethylcellulose and hydroxyethyl cellulose, more preferably said hydrophilic polymer is HMPC. Preferably, HPMC in controlled-release (CR) grade. Typical HPMC products used in controlled release matrices are METHOCEL (HPMC) K100 Premium LV, K4M Premium, K15M Premium, K100M Premium, E4M Premium, and E10M Premium CR. All of these products are available in controlled-release (CR) grades, which are specially produced, ultra-fine particle size materials. These grades differ primarily in viscosity and methoxyl substitution type.

The viscosity of the matrix forming agents (e.g. HPMC) may be of 2 to 150,000 mPa·s in a 2% by weight aqueous solution at 20° C. (determined using a Pharm. Eu. capillary viscosimeter). In a particular embodiment, said composition comprises as polymeric matrix forming agent, a HPMC with a viscosity of 80000-120000 cP, such as HPMC K100M. In a preferred embodiment the composition comprises as matrix forming agent a HPMC with a viscosity of 80-120 mPa·s, such as HPMC K100 Premium LV. The viscosity ranges provided herein correspond to apparent viscosity at 2% in water at 20° C. (determined using a Pharm. Eu. capillary viscosimeter).

The amount of the at least one hydroxyalkyl cellulose in the present oral dosage form will be determined, inter alia, by the precise rate of EE, and preferably EE and DNG, release required.

In preferred embodiments, said hydrophilic polymer, preferably a hydroxy (C1 to C6) alkyl cellulose, or the preferred embodiments described herein above, is at a concentration from 25% to 60% w/w, such as from 30% to 50% w/w, including about 30%, about 40% and about 50%, or from 45% to 55% w/w, more preferably around 50% w/w.

Acrylic polymers such as polymethacrylates are pharmacologically inactive and have good compatibility with the skin and mucosal membranes. Eudragit is a trade name of copolymers derived from esters of acrylic and methacrylic acids. Eudragit grades differ in their proportion of neutral, alkaline or acid groups resulting in different physicochemical properties. In preferred embodiments of the present invention, the gastroinsoluble polymethacrylate grade (Eudragit RL/RS) is preferred. More preferably, this acrylic resin is Eudragit RS PO.

The amount of the at least one acrylic polymer in the present oral dosage form will be determined, inter alia, by the precise rate of EE, and preferably EE and DNG, release required. In preferred embodiments, said acrylic resin is found at 10% w/w to 40% w/w, preferably at 20% w/w to 30% w/w.

In some embodiments, said matrix compositon further contains a glidant. A variety of agents may be incorporated as glidant agent (e.g., fumed silicon dioxides, Aerosil™, Aerosil™ COK84, Aerosil™ 200, etc.). Glidants enhance the pharmaceutical formulations of the invention by increasing the viscosity of solutions complementing the action of cellulose ethers (e.g., HPMCs).

In addition to the above ingredients, a sustained-release matrix may also contain suitable quantities of other excipients, e.g., diluents, lubricants, binders, granulating aids, colorants, flavorants and glidants that are conventional in the pharmaceutical art.

Suitable diluents, also known as fillers, include corn starch, microcrystalline cellulose, powdered cellulose, silicified cellulose, lactose monohydrate, anhydrous lactose, mannitol, sorbitol, sucrose, fructose, dextrose, and/or mixtures thereof. Preferably, lactose monohydrate and mannitol are used. Diluents may be presents in an amount from about 20% to about 95% by weight, preferably from 30% to 90% by weight, and more preferably from 35% to 80% by weight, even more preferably from 30% to 60%, including about 40%, about 45%, about 50%, about 55% and about 60% by weight of the total weight of the composition.

The dosage form according to the invention may also comprise a binder. The binding agent can be selected from the group consisting of hydroxypropyl cellulose, hydroxypropyl methyl cellulose, hydroxyethyl cellulose, methylcellulose, polyvinylpyrrolidone, sodium carboxymethyl cellulose, calcium carboxymethyl cellulose, and/or mixtures thereof. Preferably polyvinylpyrrolidone (e.g. Povidone K30) is used. Binders may be present in an amount from about 0.5% to about 20% by weight, preferably from 1% to 10% by weight, and more preferably from 2-7% by weight, preferably about 5% by weight of the total weight of the composition.

The dosage form according to the invention can also comprise a disintegration agent. Disintegrating agents may be selected from the group consisting of low-substituted hydroxypropyl cellulose, sodium carboxymethyl cellulose, calcium carboxymethyl cellulose, crospovidone, sodium croscarmellose, and/or mixtures thereof. Disintegrating agents may be present in an amount from about 2% to about 50% by weight, preferably from about 5% to about 45% by weight, and more preferably from 10% to 40% by weight of the total weight of the composition.

Lubricants may be selected from the group consisting of talc, alkaline earth salts of stearic acid, specially magnesium and calcium stearate, stearic acid, glycerin palmitostearate, stearyl fumarate, and/or mixtures thereof. In preferred embodiments, the lubricant is magnesium stearate. The lubricant may be present in an amount from about 0% to 5% by weight, preferably from about 1% to about 3% (e.g., about 2%) based of the total weight of the composition.

In preferred embodiments, the extended release oral dosage form of the invention comprises:
  a diluent, preferably at 30-60% w/w;
  a polymeric matrix forming agent, preferably at 10-60% w/w;
  a binder, preferably at 1-10% w/w; and
  a lubricant, preferably at 0-5% w/w.

In further preferred embodiments, said composition comprises:
  lactose (e.g. lactose monohydrate) at 35-45% w/w; preferably around 40% w/w;
  HPMC (e.g. HPMC K100) at 45-55% w/w, preferably around 50% w/w;
  povidone (e.g. povidone K30) at 2.5-7.5% w/w, preferably around 5% w/w; and
  magnesium stearate at 1.5-2.5% w/w, preferably around 2% w/w.

In even preferred embodiments, said composition comprises:
  lactose monohydrate around 40% w/w;
  HPMC K100 around 50% w/w;
  povidone K30 around 5% w/w; and
  magnesium stearate around 2% w/w.

In order to facilitate the preparation of an extended-release oral dosage form according to this invention there is provided, in a second aspect of the present invention, a process for the preparation of an extended release oral dosage form according to the present invention. In preferred embodiments, said dosage oral form is a solid form (e.g. tablets or capsules).

Methods for the manufacturing of the extended-release oral dosage form of the invention are well known in the art, such as wet granulation, dry granulation or direct compression. In wet granulation, components are typically mixed and granulated using a wet binder. The wet granulates are then sieved, dried and optionally ground prior to compressing into tablets. Dry granulation is usually described as a method of controlled crushing of precompacted powders densified by either slugging or passing the material between two counter-rotating rolls. More specifically, powdered components that may contain very fine particles are typically mixed prior to being compacted to yield hard slugs which are then ground and sieved before the addition of other ingredients and final compression to form tablets. Direct compression is generally considered to be the simplest and the most economical process for producing tablets. However, it may only be applied to materials that don't need to be granulated before tableting. Direct compression requires only two principal steps; i.e., the mixing of all the ingredients and the compression of this mixture. However, direct compression is applicable to only a relatively small number of substances as the ingredients of the tablets often need to be processed by some granulation technique to make them compressible and/or for improving their homogeneity and flowability.

Mixing and formulation of low dose drugs can be very challenging due to problems related to segregation, content uniformity and physical stability. A careful control on these factors may be necessary while manufacturing the oral dosage form described herein. Many types of equipments have been designed to facilitate mixing of low dose drugs with excipients which could also be used in the manufacturing of the extended release oral form of the invention, including but not limited to high shear granulation, ordered mixing and spray drying. Remington: The Science and Practice of Pharmacy, Pharmaceutical Press, 2013.

In a particular embodiment, said process is for obtaining a solid, extended release oral dosage form and comprises incorporating EE, preferably EE and DNG, in a extended-release matrix. This process may comprise the following steps:
  i. mixing EE and optionally DNG, with a diluent, and then mixing these together to obtain a mixture;
  ii. granulating a diluent and a polymeric matrix forming agent as described herein;
  iii. drying, optionally sieving, and mixing the granules obtained in step ii) with the mixture obtained in step i).

In preferred embodiments, said oral dosage form is a tablet and the process further comprises:
  iv. blending the mixture obtained in step iii) with a lubricant, and then compress into tablets;
  v. optionally coating the tablets obtained in step iv) with a coating agent and dry.

Alternatively, the mixture obtained in step iii) can be used to fill hard gelatin capsules.

In another embodiment, when only there is a modified or extended release of EE, a multiparticulate dose formulation as described above (e.g. pellets) may be preferred. Said process may comprise:
  a. mixing together DNG immediate release and EE extended release fraction; and
  b. fill in hard gelatin capsules or compress in tablets (e.g., see steps iv and v above).

The contraceptive composition as described herein may be suitable for administration as the daily active oral form in various administration regimens, preferred administration regimens are described herein below for contraceptive purposes but may also be used for medical purposes referred herein.

In a particular embodiment, said composition is suitable for administration as the daily active oral form in a regimen comprising the administration of the active oral form for 24 consecutive days followed by a period of 4 days of daily administration of a placebo oral form. In another particular embodiment, said composition is suitable for administration as the daily active oral form in a regimen comprising the administration of the active oral form daily for 87 consecutive days followed by a period of 4 days of daily administration of a placebo oral form or no oral form administration.

Contraceptive Uses and Methods of the Composition

Another aspect of the present invention is the use of the oral composition as described herein in contraception, in other words, it provides the oral composition as described herein as a contraceptive composition. When used for contraceptive purposes, said oral composition is used in a female subject of child-bearing age i.e. from the puberty to the menopause. Women of child-bearing age also include women in peri-menopause.

A related aspect pertains to an oral contraceptive method for a female subject in need thereof characterized in that it comprises the step of administering active daily dosage units of an oral composition as described herein to said female subject over a period of several consecutive days. In some embodiments, the active daily dosage unit is able to inhibit ovulation when daily administered to a female patient over the selected period, in preferred embodiments wherein said daily dosage unit is administered for 21 to 28 consecutive days.

In a preferred embodiment, DNG and EE are the sole contraceptive ingredients in said daily dosage units. Preferably, the dosage units do not comprise any other active ingredient.

The number of days for the administration of said daily dosage units can be 21, 22, 23, 24, 25 or 26 and the number of days free or of placebo dosages intake then 7, 6, 5, 4, 3 or 2 respectively, in the 28-day menstrual cycle. In a particular embodiment, said daily dosage unit is administered for 24 consecutive days followed by a 4-day hormone free period. In some other embodiments, the contraceptive method of the invention consists in administering "continuously" daily dosage units of the invention. Such a method does not comprise a free-contraceptive period i.e. a period in which no contraceptive or placebo pill is administered. In further embodiments the number days of administration of the daily dosage units is of 28 or a multiple of 28, for example 2 to 3 times 28. In additional embodiments, said method comprises administering the daily dosage units for an extended regimen with hormone free interval every 6 months or one year. In still further embodiments, said method comprises administering the daily dosage units from 87 to 120 consecutive days, followed by one 3 or 4-day hormone free period.

In preferred embodiments, the contraceptive method of the invention comprises two consecutive phases:
 a first phase wherein active daily dosage units of the invention are administered to the female subject over a period of 21 to 27 consecutive days and
 a second phase wherein no contraceptive composition is administered to the female subject over a period of 1 to 7 consecutive days.

As used herein a period of 1 to 7 consecutive days include periods of 1 day, of 2 consecutive days, of 3 consecutive days, of 4 consecutive days, of 5 consecutive days, of 6 consecutive days, and of 7 consecutive days.

As used herein a period of 21 to 27 consecutive days include periods of 21 consecutive days, of 22 consecutive days, of 23 consecutive days, of 24 consecutive days, of 25 consecutive days, of 26 consecutive days, and of 27 consecutive days. As mentioned above, the duration of the first phase plus the second phase is preferably 28 days.

In the first phase, the composition of active daily dose units may remain constant or may vary, with respect to the daily amount of EE and/or DNG. Preferably, it remains constant.

The second phase is a free-contraceptive period i.e. a phase during which no contraceptive ingredients is administered to the female subject. During the said second phase, daily placebo dosage units may be administered to the female subject. In some other cases, no pill is administered to the female subject. Said second phase may enable regular menstrual bleedings to occur and thus may enable to mimic the natural menstrual cycle.

As used herein, the term "active daily dosage unit" refers to physically discrete units suitable as unitary dosage which consists of a contraceptive composition as fully described hereabove in the present specification.

In some embodiments, the first phase of the contraceptive method lasts from 21 to 24 consecutive days and the second phase of the contraceptive method lasts from 4 to 7 consecutive days. In a preferred embodiment, the first phase of the contraceptive method lasts 21 days and the second phase 7. In another preferred embodiment the first phase of the contraceptive method lasts 24 days and the second phase 4.

Medical Uses and Methods of the Composition

In a further aspect, the present invention also provides an oral composition as described herein for use in the treatment of one or more of the following diseases or disorders in a female subject, preferably a premenopausal female.
 Acne
 Endometriosis
 Dysmenorrhea
 Other: dysfunctional uterine bleeding, cycle dependent complains, uterine fibroids.

In a related aspect, it refers to a method of treating one or more of the diseases or disorders mentioned above, wherein said method comprises administering to a female subject in need thereof, preferably a premenopausal female, a therapeutically effective dosage of an oral composition as described herein.

In a further related aspect, the present invention provides the use of an oral composition as described herein for the manufacturing of a medicament for the treatment of one or more of the diseases or disorders mentioned above.

Preferred embodiments and features of the kit are as described herein above for the oral composition, contraceptive methods and uses. In particular, for endometriosis treatment an extended regimen with hormone free interval every 6 months or one year may be preferred.

Kit of the Invention

In an additional aspect, the present invention also provides a kit based on the compositions described in the present application. Such a kit is particularly suitable for use in the contraceptive and medical methods as described above.

The said contraceptive kit comprises one or more packaging units. One or more packaging units includes, without being limited to, 1 packaging unit, 2 packaging units, 3 packaging units, 4 packaging units, 5 packaging units and 6 packaging units.

Each packaging unit may comprise from 21 to 28 daily active dosage units. As fully described above, each daily active dosage unit consists of a composition as described herein.

In some embodiments, the contraceptive kit is characterized in that each packaging unit comprises 28 daily dosage units and no daily dosage unit of a pharmaceutically acceptable placebo. Such a contraceptive kit is particularly appropriate to perform the contraceptive method of the invention which consists in administering "continuously" DRSP without free-contraceptive period.

In other embodiments each packaging unit comprises:
21 to 27 active daily dosage units consisting of a contraceptive composition as fully described in the present application; and
optionally, 1 to 7 daily dosage units of a pharmaceutically acceptable placebo.

Such a contraceptive kit is particularly appropriate to perform the contraceptive method of the invention which comprises
a first phase wherein active daily dosage units of the invention which do not comprise estrogen are administered to the female patient over a period of 21 to 27 consecutive days followed by
a second phase wherein no contraceptive composition is administered to the female patient over a period of 1 to 7 consecutive days.

In some other embodiments, each packaging unit of the kit comprises 24 daily dosage units comprising an effective amount of a contraceptive composition as described herein and, optionally, 4 daily dosage units of a pharmaceutically acceptable placebo.

The packaging unit as described above may have one of the conventional forms usually used for oral contraceptives. For example, the packaging unit may be a conventional blister pack comprising the appropriate number of dosage units in a sealed blister pack (e.g. an aluminium blister) with a cardboard, paperboard, foil or plastic backing and enclosed in a suitable cover. Each blister container may be conveniently numbered or marked in order to facilitate compliance. The packaging unit may contain daily dosage units in the order in which they are to be taken, i.e. starting with the first of the at least 21 dosage units that contain the combination of drospirenone optionally followed by 7 or less empty blisters or by 7 or less dosage units that comprise a pharmaceutically acceptable placebo.

The kit of the invention may comprise other appropriate components such as instructions for use.

Preferred embodiments and features of the kit are as described herein above for the oral composition, contraceptive methods and uses; and therapeutic methods and uses.

It is contemplated that any features described herein can optionally be combined with any of the embodiments of any medical or contraceptive use, composition, kit, contraceptive methods, methods of treatment, or method of manufacturing of the invention; and any embodiment discussed in this specification can be implemented with respect to any of these. It will be understood that particular embodiments described herein are shown by way of illustration and not as limitations of the invention.

All publications and patent applications are herein incorporated by reference to the same extent as if each individual publication or patent application was specifically and individually indicated to be incorporated by reference.

The use of the word "a" or "an" may mean "one," but it is also consistent with the meaning of "one or more," "at least one," and "one or more than one". The use of the term "another" may also refer to one or more. The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "comprises" also encompasses and expressly discloses the terms "consists of" and "consists essentially of". As used herein, the phrase "consisting essentially of" limits the scope of a claim to the specified materials or steps and those that do not materially affect the basic and novel characteristic(s) of the claimed invention. As used herein, the phrase "consisting of" excludes any element, step, or ingredient not specified in the claim except for, e.g., impurities ordinarily associated with the element or limitation.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "around", "approximately" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by 1, 2, 3, 4, 5, 6, 7, 8, 9, or 10%. Accordingly, the term "about" may mean the indicated value ±5% of its value, preferably the indicated value ±2% of its value, most preferably the term "about" means exactly the indicated value (±0%).

The following examples serve to illustrate the present invention and should not be construed as limiting the scope thereof.

EXAMPLES

Example 1. —Pharmacokinetic (Pk) Profile of Dienogest+Ethynilestradiol Prolonged Release (PR) Formulations The information described herein is an extract of the results of a Phase 1 clinical trial, namely an open-label, randomized, cross-over, balanced block study to evaluate the relative bioavailability from four dienogest and ethinylestradiol containing modified and immediate release formulations after repeated oral administration in healthy premenopausal women.

Materials and Methods

Objectives

The main objective of the present trial was to assess the relative bioavailability of oral test preparations containing 1 or 2 mg dienogest and 10 or 20 µg ethinylestradiol (Test IMP: dienogest/ethinylestradiol modified release tablets, manufactured by León Farma S.A., Spain) as compared to a market standard (Reference IMP: Valette™ immediate release tablet, containing dienogest 2 mg/ethinylestradiol 30 µg; company responsible for placing the product on the market: Jenapharm GmbH, Germany) after oral administration of a multiple dose once daily for 7 days under fasting conditions in four different periods, at least 7 days apart.

In order to investigate the relative bioavailability of the tested products, the pre-defined confidence intervals were calculated for the ratios (test/reference) of the primary endpoints AUC(0-τ), Cmax,ss, and Tmax,ss of dienogest and ethinylestradiol. These confidence intervals were compared with the corresponding acceptance ranges. These endpoints underwent descriptive and comparative statistical evaluation.

The secondary objective of the present trial was to investigate the safety of the preparations on the basis of safety clinical and laboratory examinations (at the beginning and at the end of the trial) and registration of adverse events and/or adverse drug reactions.

Methodology

The study was conducted as a single centre, open-label, multiple dose, crossover, randomized, four-treatment, four-period study in healthy premenopausal female volunteers of between 18 and 40 years of age and BMI within the range (including the borders) of 18.5 to 30.0 kg/m$^2$, with duration of hospitalization of approximately 26 hours (day 6 to 7) and with a real wash-out period of 7 days after the last (7th) dose in each period in all subjects.

Subjects enrolled (study population): 25
screened only: 6
randomized (safety analysis population): 19
completed: 14
data set for statistical analysis (including the available samples of the drop-outs and replacement of drop-outs): 19
data set for statistical analysis: 14

Test Products (Product, Dose and Mode of Administration)

TEST 1: Dienogest (2 mg)/Ethinylestradiol (20 µg) modified release tablet; oral/1 modified release tablet once daily for 7 days.

TEST 2: Dienogest (1 mg)/Ethinylestradiol (10 µg) modified release tablet; oral/1 modified release tablet once daily for 7 days.

TEST 3: Dienogest (2 mg)/Ethinylestradiol (10 µg) modified release tablet; oral/1 modified release tablet once daily for 7 days.

The qualitative and quantitative formulation of the tested modified release formulations, as well as the method of producing thereof is as detailed in Example 3.2 below.

Reference Product (Product, Dose and Mode of Administration)

Valette™ immediate release tablets (VALETTE™; Jenapharm GmbH & Co. KG, Germany): 2 mg dienogest and 30 µg ethinylestradiol per immediate release tablet; oral/1 immediate release tablet once daily for 7 days

Duration of Treatment

The volunteers swallowed under fasting conditions in each study period an oral daily dose of 1 modified release tablet either Test 1 or Test 2 or Test 3 IMP or 1 immediate release tablet of the Reference IMP in accordance with the randomization schedule.

Results

Fourteen volunteers completed the trial according to the protocol. The statistical BA evaluation was based on the data of 14 study completers (per protocol set).

Pharmacokinetics

The primary and secondary endpoints of the statistical analysis of dienogest and ethinylestradiol after an oral multiple dose of 1 modified release tablet (once daily for 7 days) of the Test 1, Test 2, Test 3 IMPs or 1 immediate release tablet (once daily for 7 days) of Reference drug of the 14 subjects who were subject to statistical evaluation are summarized in tables Tables 1 and 2.

TABLE 1

DIENOGEST

| Variable [unit] | geom. mean | arithm. mean | SD | CV | range | median | N |
|---|---|---|---|---|---|---|---|
| TEST 1 (2 mg dienogest and 20 µg ethinylestradiol per modified release tablet) | | | | | | | |
| AUC(0-τ) [ng * h/mL] | 716.7 | 731.6 | 158.6 | 21.7 | 542.1-1085.2 | 714.8 | 14 |
| Cmax, ss [ng/mL] | 58.2 | 59.3 | 12.3 | 20.7 | 46.6-91.4 | 55.8 | 14 |
| Tmax, ss [h] | — | 3.750 | 0.700 | 18.7 | 3.000-5.000 | 4.000 | 14 |
| TEST 2 (1 mg dienogest and 10 µg ethinylestradiol per modified release tablet) | | | | | | | |
| AUC(0-τ) [ng * h/mL] | 358.1 | 366.5 | 80.3 | 21.9 | 222.1-524.8 | 372.4 | 14 |
| Cmax, ss [ng/mL] | 28.1 | 28.6 | 5.6 | 19.7 | 20.0-40.9 | 26.8 | 14 |
| Tmax, ss [h] | — | 3.857 | 0.745 | 19.3 | 3.000-5.000 | 4.000 | 14 |
| TEST 3 (2 mg dienogest and 10 µg ethinylestradiol per modified release tablet) | | | | | | | |
| AUC(0-τ) [ng * h/mL] | 721.1 | 735.0 | 154.3 | 21.0 | 569.2-1006.5 | 719.1 | 14 |
| Cmax, ss [ng/mL] | 55.4 | 56.2 | 10.1 | 17.9 | 41.7-76.4 | 56.0 | 14 |
| Tmax [h] | — | 3.754 | 0.752 | 20.0 | 2.500-5.000 | 4.000 | 14 |
| REFERENCE (2 mg dienogest and 30 µg ethinylestradiol per immediate release tablet) | | | | | | | |
| AUC(0-τ) [ng * h/mL] | 707.2 | 720.3 | 140.9 | 19.6 | 466.8-1000.2 | 731.1 | 14 |

TABLE 1-continued

DIENOGEST

| Variable [unit] | geom. mean | arithm. mean | SD | CV | range | median | N |
|---|---|---|---|---|---|---|---|
| Cmax, ss [ng/mL] | 74.6 | 75.4 | 12.5 | 16.5 | 60.8-109.0 | 74.0 | 14 |
| Tmax, ss [h] | — | 1.321 | 0.805 | 60.9 | 0.333-3.000 | 1.000 | 14 |

TABLE 2

ETHINYLESTRADIOL

| Variable [unit] | geom. mean | arithm. mean | SD | CV | range | median | N |
|---|---|---|---|---|---|---|---|
| TEST 1 (2 mg dienogest and 20 μg ethinylestradiol per modified release tablet) | | | | | | | |
| AUC(0-τ) [pg * h/mL] | 683.3 | 706.3 | 196.4 | 27.8 | 465.4-1221.1 | 691.4 | 14 |
| Cmax, ss [pg/mL] | 59.9 | 63.6 | 23.3 | 36.6 | 33.3-112.0 | 60.0 | 14 |
| Tmax, ss [h] | — | 3.754 | 1.242 | 33.1 | 2.000-6.033 | 4.000 | 14 |
| TEST 2 (1 mg dienogest and 10 μg ethinylestradiol per modified release tablet) | | | | | | | |
| AUC(0-τ) [pg * h/mL] | 342.4 | 351.9 | 90.0 | 25.6 | 239.6-587.9 | 331.9 | 14 |
| Cmax, ss [pg/mL] | 31.2 | 32.3 | 9.5 | 29.5 | 23.1-56.4 | 29.9 | 14 |
| Tmax, ss [h] | — | 3.571 | 0.805 | 22.5 | 2.500-5.000 | 3.500 | 14 |
| TEST 3 (2 mg dienogest and 10 μg ethinylestradiol per modified release tablet) | | | | | | | |
| AUC(0-τ) [pg * h/mL] | 326.2 | 338.4 | 99.0 | 29.3 | 188.0-590.7 | 330.0 | 14 |
| Cmax, ss [pg/mL] | 30.4 | 33.2 | 15.8 | 47.5 | 15.9-75.5 | 28.4 | 14 |
| Tmax, ss [h] | — | 3.468 | 0.746 | 21.5 | 2.000-5.000 | 3.500 | 14 |
| REFERENCE (2 mg dienogest and 30 μg ethinylestradiol per immediate release tablet) | | | | | | | |
| AUC(0-τ) [pg * h/mL] | 1030.5 | 1072.8 | 345.2 | 32.2 | 636.8-2055.1 | 974.0 | 14 |
| Cmax, ss [pg/mL] | 129.0 | 135.2 | 44.9 | 33.2 | 78.2-250.0 | 132.5 | 14 |
| Tmax, ss [h] | — | 1.345 | 0.504 | 37.5 | 0.667-2.000 | 1.250 | 14 |

The concentration-time curve of dienogest after administration of an oral multiple dose of 1 modified release tablet of the Test 1, Test 2, Test 3 IMPs and 1 immediate release tablet of Reference drug once daily for 7 days are to be found in FIG. 1 for the all preparations (arithmetic means).

Figure 2:
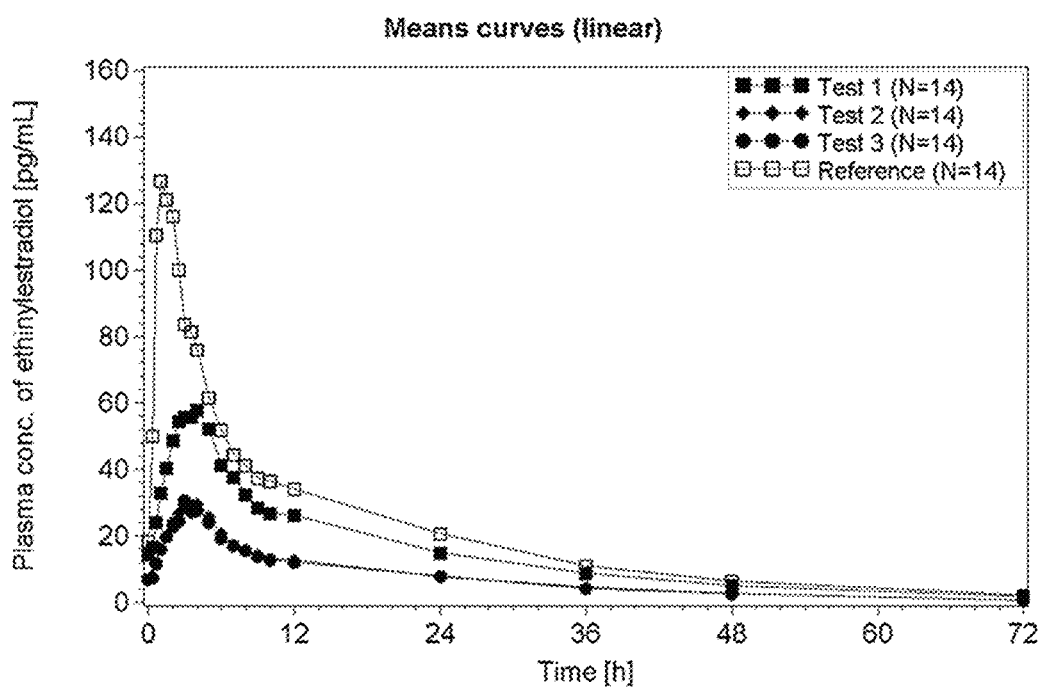
FIG. 2. Mean (arithmetic) ethinylestradiol plasma concentration-time profile (linear) after oral administration of a multiple dose once daily for 7 days.

The concentration-time curve of ethinylestradiol after administration of an oral multiple dose of 1 modified release tablet of the Test 1, Test 2, Test 3 IMPs and 1 immediate release tablet of the Reference drug are to be found in FIG. 2 for all preparations (arithmetic means).

Figure 3:
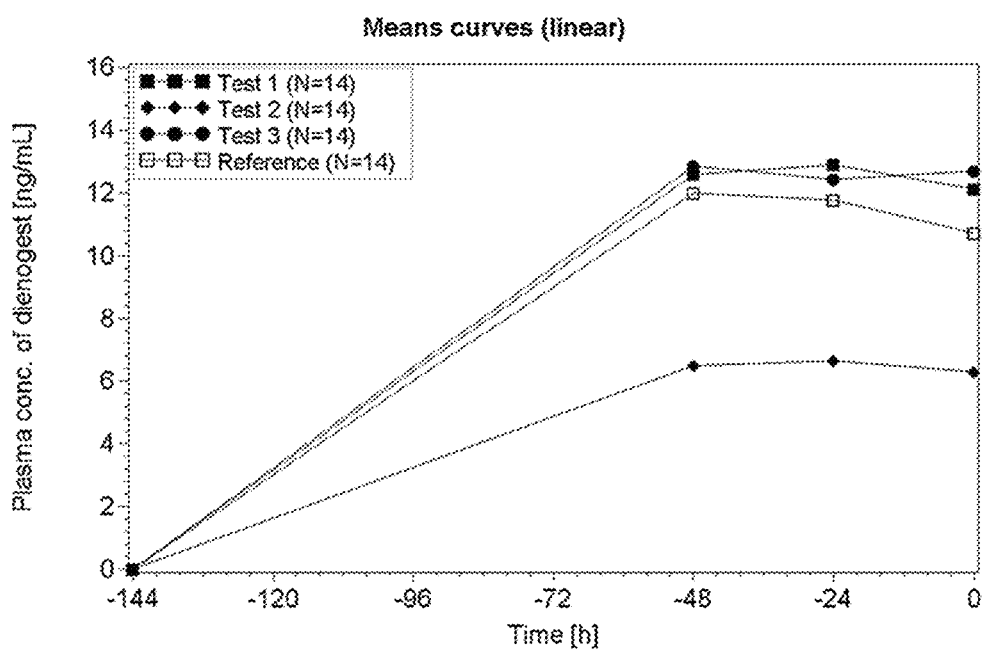
FIG. 3. Dienogest plasma concentration-time profile on dosing days 1 to 7 (before kinetic day 7). Legend: TEST 1: 2 mg dienogest and 20 µg ethinylestradiol per modified release tablet; TEST 2: 1 mg dienogest and 10 µg ethinylestradiol per modified release tablet; TEST 3: 2 mg dienogest and 10 µg ethinylestradiol per modified release tablet; REFERENCE: 2 mg dienogest and 30 µg ethinylestradiol per immediate release tablet FIG. 4. Ethinylestradiol plasma concentration-time profile on dosing days 1 to 7 (before kinetic day 7). Legend: TEST 1: 2 mg dienogest and 20 µg ethinylestradiol per modified release tablet; TEST 2: 1 mg dienogest and 10 µg ethinylestradiol per modified release tablet; TEST 3: 2 mg dienogest and 10 µg ethinylestradiol per modified release tablet; REFERENCE: 2 mg dienogest and 30 µg ethinylestradiol per immediate release tablet.
Figure 4:
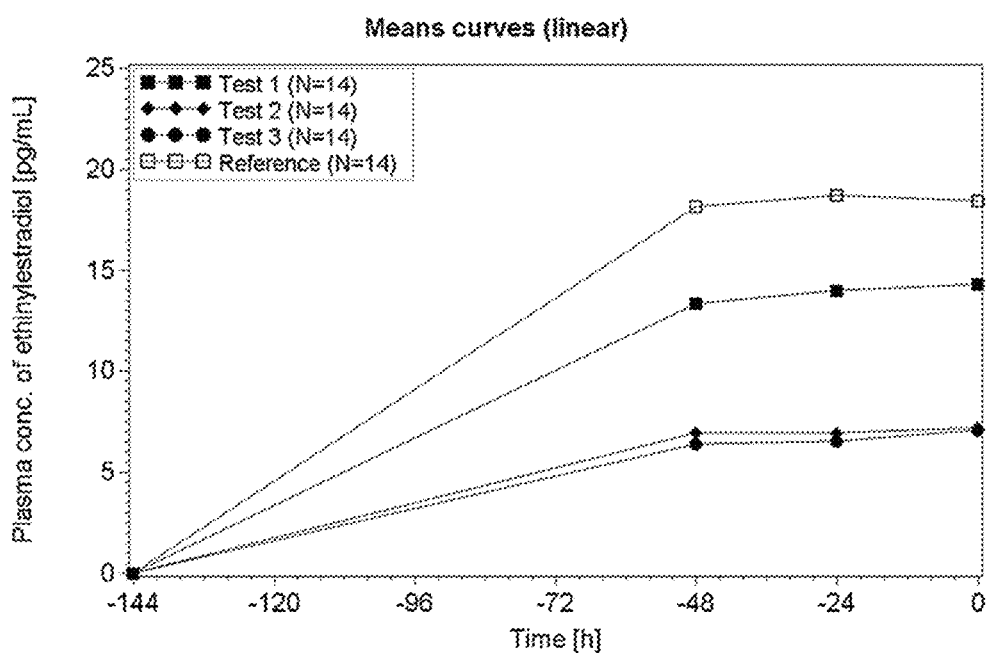
Figure 5:
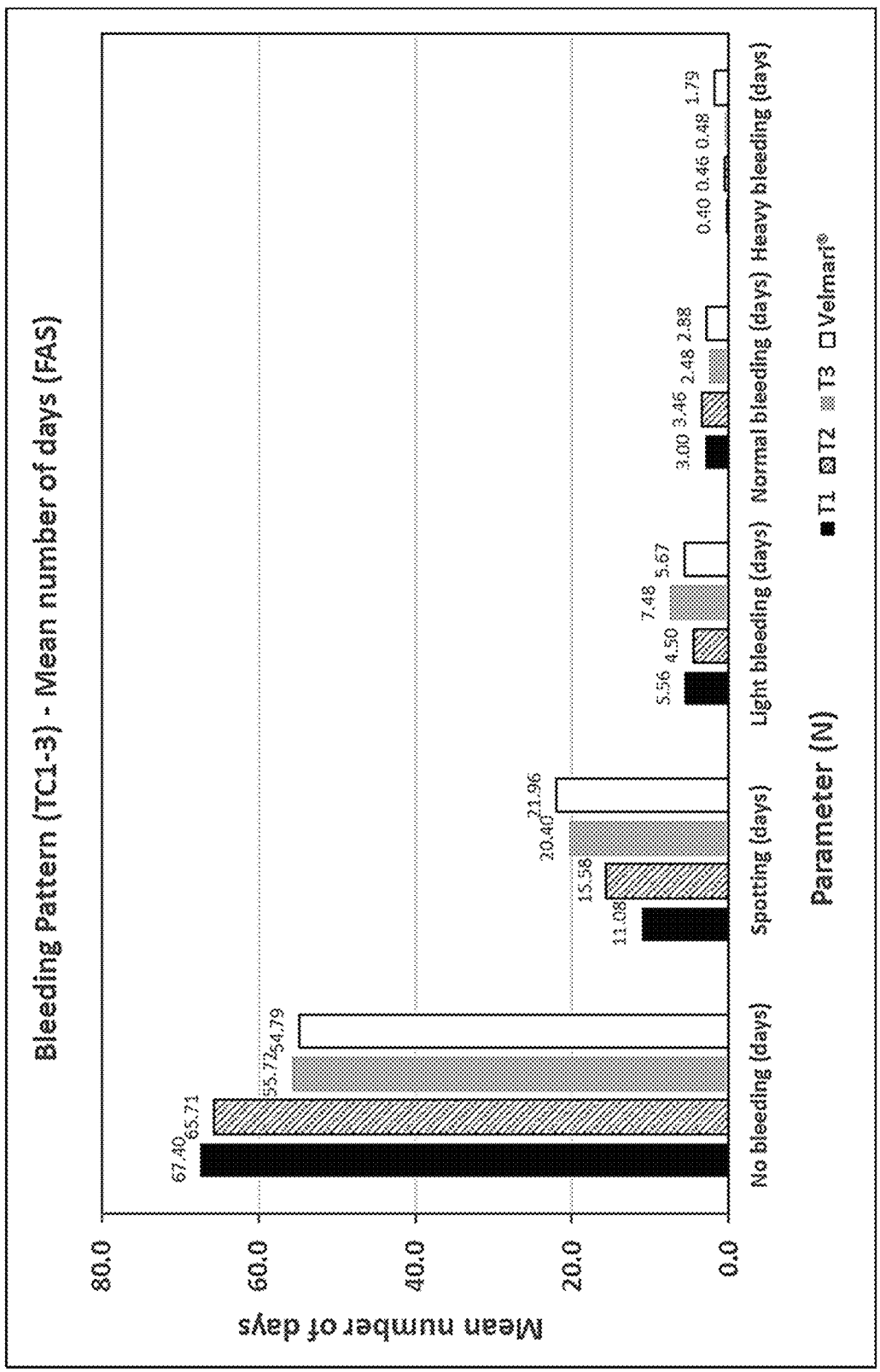
FIG. 5. Bleeding Pattern TC 1 to TC 3, Mean Number of Days (Full Analysis Set). Abbreviations: DNG=dienogest; EE=ethinyl estradiol; FAS=full analysis set; N=number of subjects; T1=EE/DNG 10 µg/1 mg; T2=EE/DNG 10 µg/2 mg; T3=EE/DNG 20 µg/2 mg; TC=treatment cycle; Velmari®=Velmari Langzyklus 0.02/3 mg tablets (EE 20 µg/drospirenone 3 mg).
Figure 6:
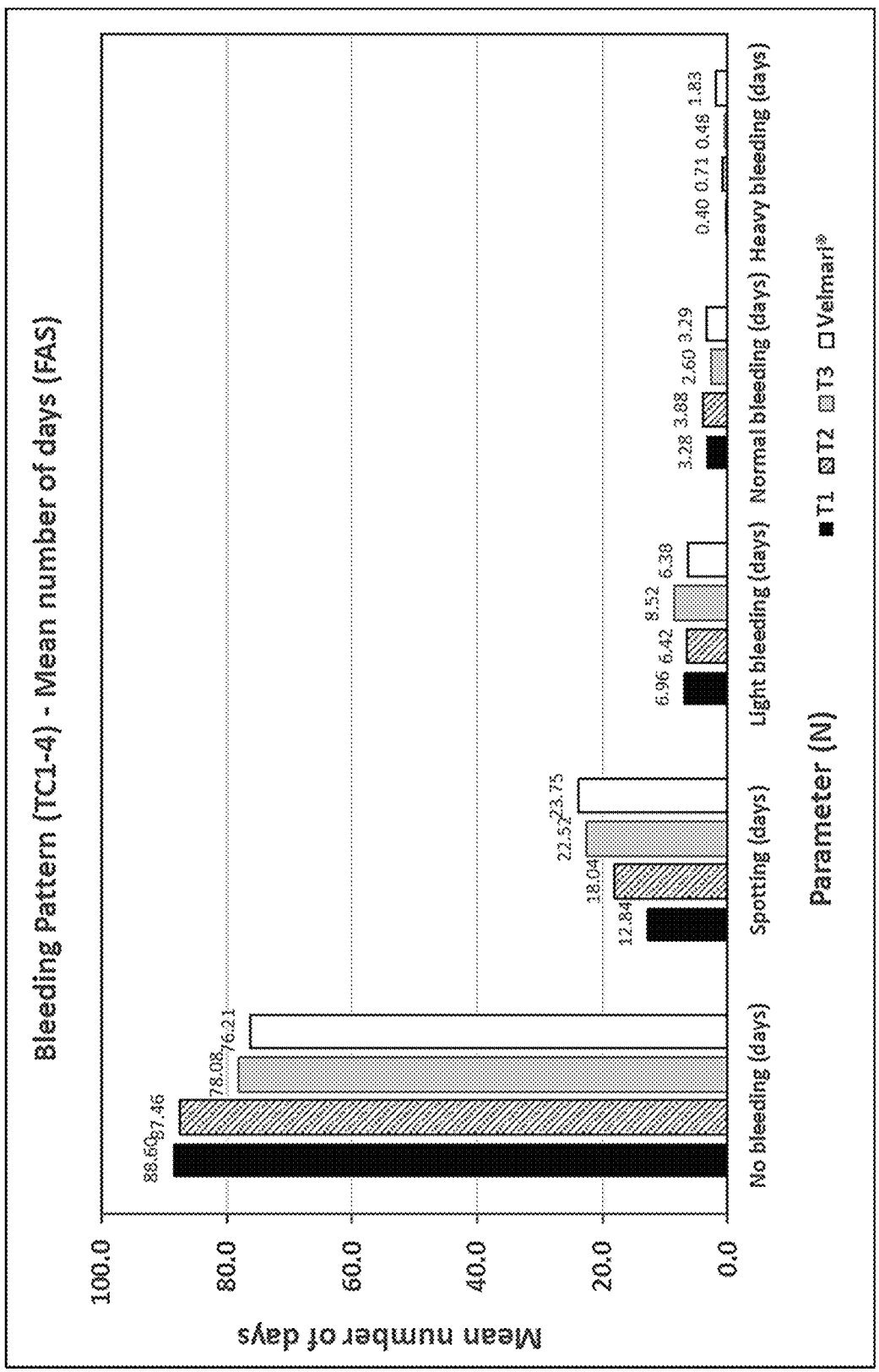
FIG. 6. Bleeding Pattern TC 1 to TC 4, Mean Number of Days (Full Analysis Set). Abbreviations: DNG=dienogest; EE=ethinyl estradiol; FAS=full analysis set; N=number of subjects; T1=EE/DNG 10 µg/1 mg; T2=EE/DNG 10 µg/2 mg; T3=EE/DNG 20 µg/2 mg; TC=treatment cycle; Velmari®=Velmari Langzyklus 0.02/3 mg tablets (EE 20 µg/drospirenone 3 mg).

The achieving of steady-state for both dienogest and ethinylestradiol concentrations before the 7th dose is presented in text FIGS. 3 and 4.

Safety:

The 3 Test formulations and the Reference drug were equally well tolerated. The pattern of almost all AEs is in the line with what has to be expected after administration of dienogest and ethinylestradiol (mentioned in the SmPC of the reference IMP Valette™)

Overall Study Conclusions

In this study, all tested formulations containing dienogest and ethinylestradiol were safe and well tolerated after multiple dose of once daily administration for 7 days in healthy premenopausal females. The tolerability of the three investigational prolonged release formulations was comparable to the reference product.

Attainment of steady-state: pre-dose blood samples were taken on days 1, 5, 6, and 7 of dosing. For all products and for both analytes, the pre-dose levels did not increase after day 5.

After repeated daily intake over 7 days of administration, the main pharmacokinetic characteristics of the three Test PR formulations—Dienogest/ethinylestradiol modified release tablets were:
- Tmax was shifted from 1.5 hours to approximately 4 hours in the PR formulations.
- AUC0-24 h was strictly proportional compared to the immediate release reference product.
- Peak Through Fluctuations were reduced in the PR formulations compared to immediate release reference product (Cmax was reduced by approx. 25% and Cmin was slightly higher in the PR formulations).

Example 2. —Contraceptive Efficacy of Dienogest+Ethynilestradiol PR Formulations The information described herein is an extract of the results of a single center, phase II, open label randomized clinical trial to evaluate the inhibition of ovulation of three prolonged release formulations containing a combination of dienogest and ethinyl estradiol versus a flexible regimen contraceptive containing drospirenone 3 mg and ethinyl estradiol 20 μg in 100 healthy women.

Materials and Methods

Objectives

The primary objective was the inhibition of ovarian activity (Hoogland score) of oral modified release preparations containing 1 or 2 mg dienogest and 10 or 20 µg ethinylestradiol compared with the immediate release oral contraceptive Velmari® (EE 0.02 mg/drospirenone 3 mg) in Treatment Cycle (TC) 1 and TC 4.

The bleeding pattern; serum levels of progesterone, estradiol (E2), follicle-stimulating hormone (FSH), and luteinizing hormone (LH); safety and tolerability; and the Landgren score if an ovulation had been observed sonographically in TC 1 or TC 4 were secondary objectives of the study.

Methodology

Healthy women were randomized in a 1:1:1:1 ratio to receive 1 of 4 unblinded treatments: ethinyl estradiol (EE)/dienogest (DNG) 10 µg/1 mg, or EE/DNG 10 µg/2 mg, or EE/DNG 20 µg/2 mg, or Velmari® Langzyklus 0.02/3 mg tablets (EE 20 µg/drospirenone 3 mg).

Number of Subjects (Planned and Analyzed)

Planned: 100; Actual: 100; Completed: 84; Analyzed: 100.

Determination of Sample Size

There was no formal sample size calculation. The sample size was set to 25 subjects per group (total 100 subjects allocated in the trial) and was based on methodology of DNG-mediated inhibition of ovulation as described in the literature (Klipping et al 2012).

Diagnosis and Main Criteria for Inclusion

The study sample were healthy women (18-35 years, inclusive) with a history of regular cycles and no evident gynecological abnormalities. Women with conditions or characteristics that might have had an impact on the aims of the study or meant a safety risk for the subject were excluded. In particular, pregnancy, a likelihood of residual pharmaceutical hormones in the body, or a history of thrombophlebitis, venous or arterial thromboembolic diseases led to exclusion.

Test and Reference Products (Product, Dose and Mode of Administration)

T1: EE/DNG 10 µg/1 mg
T2: EE/DNG 10 µg/2 mg
T3: EE/DNG 20 µg/2 mg
T4: Velman® Langzyklus 0.02/3 mg tablets (EE 20 µg/drospirenone 3 mg)

For oral administration. One tablet/day.

Subjects received an investigational medicinal product (IMP) kit containing 4 blisters of 24 tablets to cover the 87-day treatment period. On Day 91, subjects taking test products were given 1 blister of 28 tablets and subjects taking Velmari® were given 2 blisters each containing 24 tablets.

Both test and reference products were manufactured and packaged by Laboratorios León Farma, S.A. (León, Spain).

The qualitative and quantitative formulation of the tested modified release formulations, as well as the method of producing thereof is as detailed in Example 3.2 below.

Duration of Treatment

Treatment phase (TC1 to TC4): 119 days. TC1 to TC3 corresponds to a first treatment period (extended) 87 days intake+4 hormone-free days (91); and TC 4 to a second treatment period of 24 days intake+4 hormone-free days. TC1 corresponds to days 1 to 27.

Statistical Methods

This was an exploratory study. All data were summarized with sample statistics or frequency tables as appropriate.

Results

One hundred subjects were randomized and received at least 1 dose of IMP, and 84 subjects completed the study.

Efficacy Results

Primary Efficacy Endpoint:

Inhibition of ovulation was measured using the Hoogland score (Hoogland and Skouby 1993), which reflects the ovarian status, during TC 1 and TC 4, based on the observations at the scheduled visits.

The Hoogland score combines follicle size in mm and progesterone/estradiol serum concentrations in nmol/L. The scoring system is detailed in Table 3

TABLE 3

Hoogland Score Evaluation

| Score | Size of Largest Follicle | Progesterone | | Estradiol | |
|---|---|---|---|---|---|
| 1: No activity | ≤10 mm | — | — | — | — |
| 2: Potential activity | >10 mm | — | — | — | — |
| 3: Nonactive FLS | >13 mm | — | — | ≤27.2 pg/mL | ≤0.1 nmol/L |
| 4: Active FLS | >13 mm | ≤1.6 ng/ml | ≤5 nmol/L | >27.2 pg/mL | >0.1 nmol/L |
| 5: LUF | >13 mm persisting | >1.6 ng/ml | >5 nmol/L | >27.2 pg/mL | >0.1 nmol/L |
| 6: Ovulation | >13 mm ruptured | >1.6 ng/ml | >5 nmol/L | >27.2 pg/mL | >0.1 nmol/L |

Abbreviations:
FLS = follicle-like structure;
LUF = luteinized unruptured follicle The maximum Hoogland score observed during the study was used for the efficacy assessment. Three categories were defined based on the Hoogland score:

1 or 2: no or minimum ovarian activity
3 or 4: residual ovarian activity
5 or 6: high ovarian activity including ovulation A Hoogland score 1 to 4 was defined as "inhibition of ovulation" for the efficacy assessment. Based on this definition, the inhibition rate in the treatment groups T3 and Velmari® was 100% in TC 1 and TC 4. For T2, the inhibition rates were 100% and 95.5% in TC 1 and TC 4; for T1, the inhibition rates were 96.0% and 90.9% in TC 1 and TC 4 (Table 4).

TABLE 4

| TC No. | Inhibition | T1 N = 25 n (%) | T2 N = 24 n (%) | T3 N = 25 n (%) | Velmari® N = 24 n (%) |
|---|---|---|---|---|---|
| TC 1 | No | 1 (4.0) | 0 | 0 | 0 |
|  | Yes | 24 (96.0) | 24 (100.0) | 25 (100.0) | 24 (100.0) |
| TC 4 | No | 2 (9.1) | 1 (4.5) | 0 | 0 |
|  | Yes | 20 (90.9) | 21 (95.5) | 22 (100.0) | 20 (100.0) |

Secondary Efficacy Endpoints:
Landgren Score

The Landgren score was determined in TC 1 and TC 4 only if an ovulation was suspected in the TVU examination and if the corresponding Hoogland score was 5 or 6.

According to Landgren (Landgren et al 1980), a normal ovulation can be verified by a progesterone level of >16 nmol/L on a minimum of 5 consecutive days. For the purpose of this study, the Landgren score was positive if in 3 progesterone measurements within 5 days the progesterone was >16 nmol/L.

The Landgren score was determined 5 times (T1: 4 cases; T2: 1 case). It was positive in one T1 subject during TC 4 and negative in all other cases.

Bleeding Pattern

The Bleeding Pattern is not an absolute value but relative to other contraceptives and doses. The trial was double-blind and Velmari® was used herein for comparative purposes. Subjects noted the occurrence of vaginal bleeding in a subject diary as none, spotting, light, normal, or heavy bleeding. For the analysis, the following treatment periods were considered and tabulated separately: TC 1 (Day 1-24), TC 4 (Day 92-119), TC 1 to TC 3 (Day 1-91), and TC 1 to TC 4 (Day 1-119). Summary data of TC 4 and TC 1 to TC 3 are shown in Table 5.

"No bleeding" was recorded for the majority of days in all treatment groups, followed by "spotting." Only a small proportion of days were recorded as light, normal, or heavy bleeding (in descending order) for all treatment groups.

The bleeding pattern was least favorable in the Velmari® group with a mean value of only 76 bleeding-free days, compared with 78 days for T3, 87 days for T2, and 89 days for T1 (TC 1 to TC 4 inclusive). In TC 4, however, values converged towards 23 to 24 days for all groups.

TABLE 5

Bleeding Pattern (Full Analysis Set)

| | Bleeding Category | | T1 N = 25 | T2 N = 25 | T3 N = 25 | Velmari ® N = 25 | Total N = 100 |
|---|---|---|---|---|---|---|---|
| TC 1 | None (days) | Mean ± SD[1] | 18.7 ± 5.1 | 17.0 ± 5.9 | 13.7 ± 7.5 | 16.7 ± 6.2 | 16.5 ± 6.4 |
| | | Min-Max | 7-24 | 0-24 | 1-25 | 1-24 | 0-25 |
| | Spotting (days) | Mean ± SD | 3.2 ± 3.7 | 4.9 ± 5.5 | 7.9 ± 6.1 | 5.2 ± 5.7 | 5.3 ± 5.5 |
| | | Min-Max | 0-13 | 0-23 | 0-23 | 0-21 | 0-23 |
| | Light (days) | Mean ± SD | 2.7 ± 2.2 | 2.0 ± 1.3 | 3.0 ± 3.0 | 2.5 ± 2.0 | 2.6 ± 2.2 |
| | | Min-Max | 0-9 | 0-5 | 1-12 | 0-7 | 0-12 |
| | Normal (days) | Mean ± SD | 2.1 ± 1.4 | 2.5 ± 1.5 | 2.0 ± 1.1 | 1.9 ± 1.2 | 2.1 ± 1.3 |
| | | Min-Max | 0-5 | 1-8 | 0-4 | 0-5 | 0-8 |
| | Heavy (days) | Mean ± SD | 0.4 ± 0.8 | 0.3 ± 0.7 | 0.5 ± 0.9 | 0.8 ± 1.0 | 0.5 ± 0.9 |
| | | Min-Max | 0-3 | 0-2 | 0-3 | 0-4 | 0-4 |
| | Number of episodes | Mean ± SD | 1.5 ± 0.6 | 1.4 ± 0.6 | 1.8 ± 0.7 | 1.5 ± 0.6 | 1.6 ± 0.6 |
| | | Min-Max | 1-3 | 1-3 | 1-3 | 1-3 | 1-3 |
| TC 4 | None (days) | Mean ± SD | 24.1 ± 3.7 | 22.7 ± 5.3 | 24.3 ± 4.0 | 23.4 ± 5.8 | 23.6 ± 4.8 |
| | | Min-Max | 17-28 | 6-28 | 9-28 | 0-28 | 0-28 |
| | Spotting (days) | Mean ± SD | 2.0 ± 2.4 | 2.6 ± 2.5 | 2.3 ± 3.5 | 2.0 ± 2.6 | 2.2 ± 2.7 |
| | | Min-Max | 0-9 | 0-8 | 0-16 | 0-9 | 0-16 |
| | Light (days) | Mean ± SD | 1.6 ± 2.0 | 2.0 ± 2.4 | 1.1 ± 1.2 | 0.8 ± 0.9 | 1.4 ± 1.8 |
| | | Min-Max | 0-7 | 0-8 | 0-4 | 0-3 | 0-8 |
| | Normal (days) | Mean ± SD | 0.3 ± 0.9 | 0.4 ± 0.9 | 0.1 ± 0.3 | 0.4 ± 0.6 | 0.3 ± 0.7 |
| | | Min-Max | 0-4 | 0-3 | 0-1 | 0-2 | 0-4 |
| | Heavy (days) | Mean ± SD | 0 | 0.3 ± 1.1 | 0 | 0.0 ± 0.2 | 0.1 ± 0.5 |
| | | Min-Max | 0 | 0-5 | 0 | 0-1 | 0-5 |
| | Number of episodes | Mean ± SD | 1.2 ± 0.9 | 1.5 ± 1.3 | 1.4 ± 0.8 | 1.3 ± 0.8 | 1.4 ± 1.0 |
| | | Min-Max | 0-3 | 0-6 | 0-3 | 0-3 | 0-6 |
| TC 1-3 | None (days) | Mean ± SD | 67.4 ± 18.0 | 65.7 ± 21.1 | 55.7 ± 20.1 | 54.8 ± 27.0 | 60.9 ± 22.2 |
| | | Min-Max | 20-87 | 0-87 | 12-91 | 1-87 | 0-91 |
| | Spotting (days) | Mean ± SD | 11.1 ± 11.1 | 15.6 ± 16.0 | 20.4 ± 14.1 | 22.0 ± 20.2 | 17.2 ± 16.0 |
| | | Min-Max | 0-51 | 0-61 | 0-48 | 0-64 | 0-64 |
| | Light (days) | Mean ± SD | 5.6 ± 4.2 | 4.5 ± 4.1 | 7.5 ± 6.9 | 5.7 ± 5.4 | 5.8 ± 5.3 |
| | | Min-Max | 1-15 | 0-19 | 1-21 | 0-24 | 0-24 |
| | Normal (days) | Mean ± SD | 3.0 ± 2.0 | 3.5 ± 2.5 | 2.5 ± 1.5 | 2.9 ± 2.0 | 3.0 ± 2.0 |
| | | Min-Max | 0-7 | 1-12 | 0-5 | 1-7 | 0-12 |
| | Heavy (days) | Mean ± SD | 0.4 ± 0.9 | 0.5 ± 1.0 | 0.5 ± 0.9 | 1.8 ± 3.6 | 0.8 ± 2.0 |
| | | Min-Max | 0-3 | 0-3 | 0-3 | 0-16 | 0-16 |
| | Number of episodes | Mean ± SD | 3.8 ± 1.9 | 3.8 ± 2.1 | 4.3 ± 2.1 | 3.3 ± 1.6 | 3.8 ± 1.9 |
| | | Min-Max | 1-8 | 1-7 | 1-12 | 1-6 | 1-12 |

Abbreviations: DNG = dienogest; EE = ethinyl estradiol; Max = maximum; Min = minimum; N = number of subjects; T1 = EE/DNG 10 µg/1 mg; T2 = EE/DNG 10 µg/2 mg; T3 = EE/DNG 20 µg/2 mg; TC = treatment cycle; Velmari ® = Velmari Langzyklus 0.02/3 mg tablets (EE 20 µg/drospirenone 3 mg)
[1]Mean and SD values are rounded to 1 decimal place Differences between treatment groups were largest for the categories "no bleeding" and "spotting." Intergroup differences for "light," "normal," and "heavy" bleeding differed by no more than 1 day per treatment cycle.

In TC4, the number of bleeding free days was very similar between all groups. The number of bleeding events classified under "light", "normal" and "heavy" for T3 were equal or lower than T1 or T2. Only the number of "spotting" events was higher in T3 than T1. Finally, the number of episodes differed only in 0.2 between T1 and T3. Thus, it may be concluded that in TC4 there were no significant differences between the prolonged release formulations.

During the TC1-TC3 period, a slightly more favorable profile was observed for the PR formulations with respect to the number of "heavy" bleeding, as well as for "spotting" and "no bleeding" days.

As a conclusion, with respect to the bleeding pattern no significant differences were found between the different doses of the PR formulations and these have a more favorable profile than the reference product, especially during TC1-TC3.

Safety and Tolerability

All products were safe and reasonably tolerable. More than four-fifth of subjects experienced at least 1 IMP-related AE, most of mild or moderate intensity. Headache, lower abdominal pain, and breast discomfort were the most frequent IMP-related AEs. The single serious AE reported in this study was unrelated to the IMP and occurred under Velmari® treatment. The safety data did not reveal any clinically meaningful differences between treatment groups. Details are presented in Table 6.

TABLE 6

| Event | T1 N = 25 n (%) | T1 N = 25 Events | T2 N = 25 n (%) | T2 N = 25 Events | T3 N = 25 n (%) | T3 N = 25 Events | Velmari® N = 25 n (%) | Velmari® N = 25 Events |
|---|---|---|---|---|---|---|---|---|
| All AE | 25 (100.0) | 173 | 24 (96.0) | 144 | 25 (100.0) | 141 | 25 (100.0) | 153 |
| Pretreatment AE | 0 (0.0) | 0 | 0 (0.0) | 0 | 1 (4.0) | 1 | 1 (4.0) | 1 |
| TEAE | 25 (100.0) | 173 | 24 (96.0) | 144 | 25 (100.0) | 140 | 25 (100.0) | 152 |
| ADR | 22 (88.0) | 94 | 20 (80.0) | 67 | 21 (84.0) | 70 | 21 (84.0) | 72 |
| Serious TEAE | 0 (0.0) | 0 | 0 (0.0) | 0 | 0 (0.0) | 0 | 1 (4.0) | 1 |
| Serious ADR | 0 (0.0) | 0 | 0 (0.0) | 0 | 0 (0.0) | 0 | 0 (0.0) | 0 |
| TEAE leading to IMP withdrawal | 2 (8.0) | 2 | 1 (4.0) | 1 | 1 (4.0) | 1 | 3 (12.0) | 4 |

Example 3.—EE 0.02 mg/DNG 2 mg Extended Release Formulations

Example 3.1. Dissolution Profiles of Alternative Matrix Forming Polymers at Various Concentrations (w/w %)

3.1. Lactose—Eudragit RS PO/Formulation 1

Table 7 shows the qualitative and quantitative composition of Formulation 1.

TABLE 7

| | Formulation 1 | |
|---|---|---|
| Material | mg/tablet | % |
| Dienogest | 2.00 | 4.00 |
| Ethinyl estradiol | 0.02 | 0.04 |
| Lactose monohydrate | 35.48 | 70.96 |
| Eudragit RS PO | 10.00 | 20.00 |
| Povidone K30 | 1.50 | 3.00 |
| Ethanol 96% | * | |
| Water | * | |
| Magnesium stearate | 1.00 | 2.00 |
| Total | 50.0 | 100 |

* Evaporated during the process

Manufacturing Process:

Eudragit RS PO and lactose (1$^{st}$ fraction, 16 mg) were granulated with the binder solution: Water, Ethanol 96%, Povidone K30. The granules obtained were mixed and blended with dienogest, Ethinyl estradiol and the remaining lactose (2$^{nd}$ fraction, remaining lactose). The granules were lubricated with Magnesium stearate and compressed to round, biconvex tablets, diameter 5.0 mm, average weight 50.0 mg.

Figure 7A:
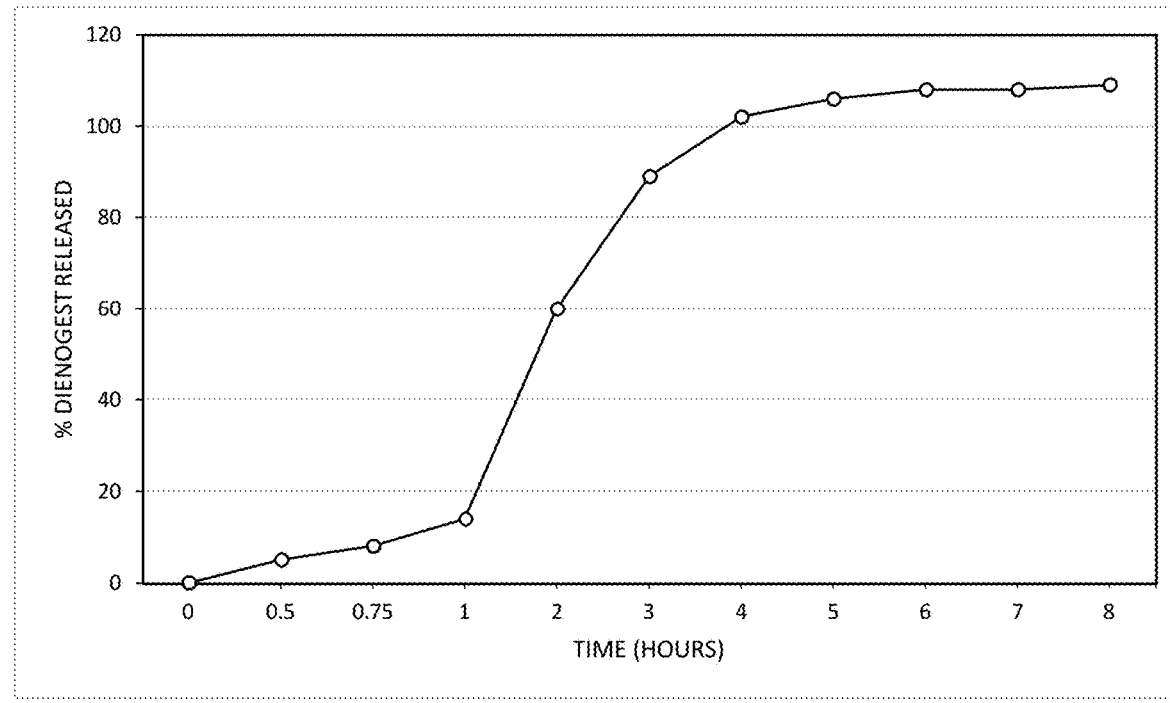
FIG. 7A. DNG dissolution profile of formulation 1.
Figure 7B:
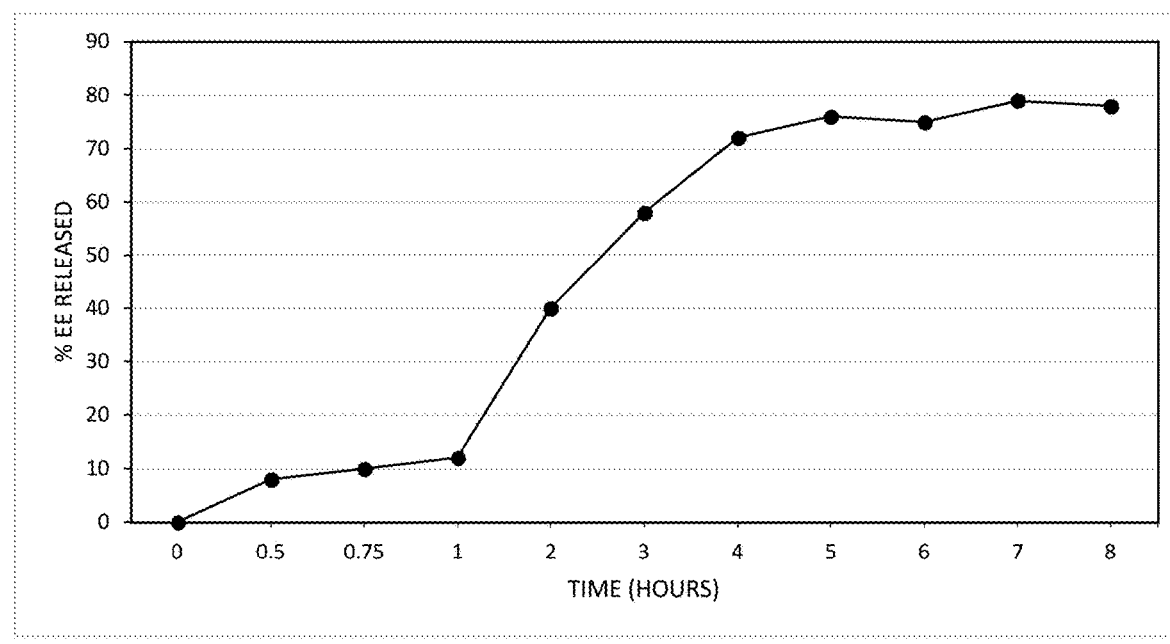
FIG. 7B. EE dissolution profile of formulation 1.

The dissolution profile of dienogest and EE in formulation 1 is shown in FIGS. 7A and 7B, respectively.

The dissolution method used for releasing Dienogest/ Ethinyl Estradiol 2.00 mg/0.02 mg, extended release tablets is as follows:

| Apparatus: | USP 1 (baskets) |
|---|---|
| Medium: | Water, purified |
| Speed: | 75 rpm |
| Volume: | 900 mL |
| Temperature: | 37° C. ± 0.5° C. |

3.2. Mannitol—Eudragit RS PO/Formulations 2 and 3

Formulations 2 and 3 show the effect of Eudragit RS PO at concentrations of 30% and 40% in the dissolution profile of both dienogest and ethinyl estradiol. The quantity of Eudragit RS PO was adjusted by changing the quantity of Mannitol. Table 8 shows the qualitative and quantitative composition of Formulations 2 and 3.

TABLE 8

| | Formulation 2 | | Formulation 3 | |
|---|---|---|---|---|
| Material | mg/tablet | % | mg/tablet | % |
| Dienogest | 2.00 | 4.00 | 2.00 | 4.00 |
| Ethinyl estradiol | 0.02 | 0.04 | 0.02 | 0.04 |
| Mannitol | 29.48 | 58.96 | 24.48 | 48.96 |
| Eudragit RS PO | 15.00 | 30.00 | 20.00 | 40.00 |
| Povidone K30 | 2.50 | 5.00 | 2.50 | 5.00 |
| Ethanol 96% | * | * | * | * |
| Water | * | * | * | * |
| Magnesium stearate | 1.00 | 2.00 | 1.00 | 2.00 |
| Total | 50.0 | 100 | 50.0 | 100 |

* Evaporated during the process

Manufacturing Process:

Eudragit RS PO and mannitol (1$^{st}$ fraction, 16 mg) were granulated with the binder solution: Water, Ethanol 96%, Povidone K30. The granules obtained were mixed and blended with dienogest, Ethinyl estradiol and the remaining lactose (2$^{nd}$ fraction). The granules were lubricated with Magnesium stearate and compressed to round, biconvex tablets, diameter 5.0 mm, average weight 50.0 mg.

Figure 8A:
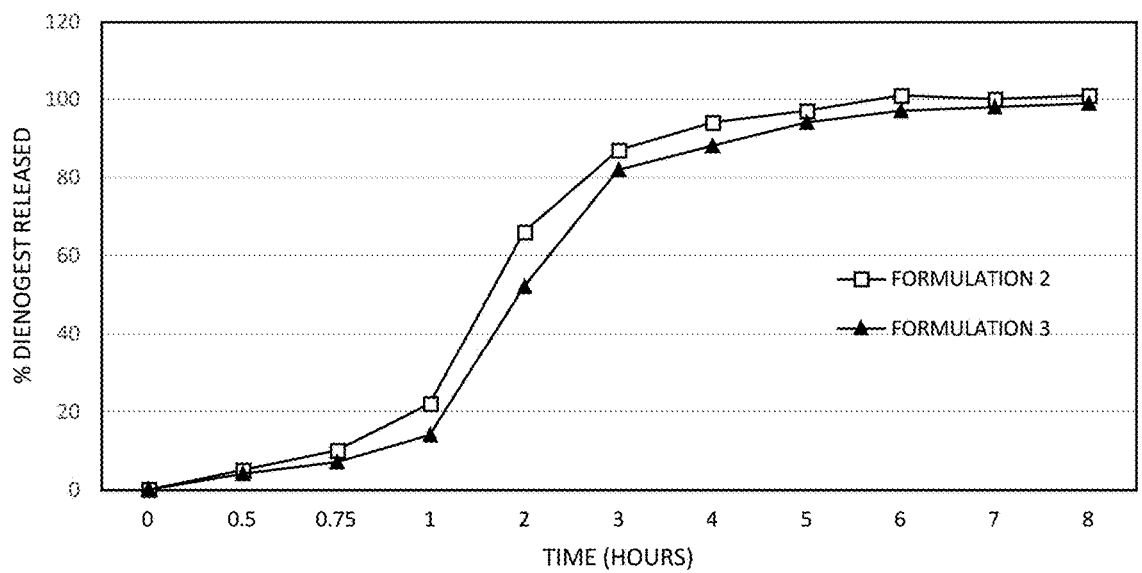
FIG. 8A. DNG dissolution profiles of formulations 2 and 3.
Figure 8B:
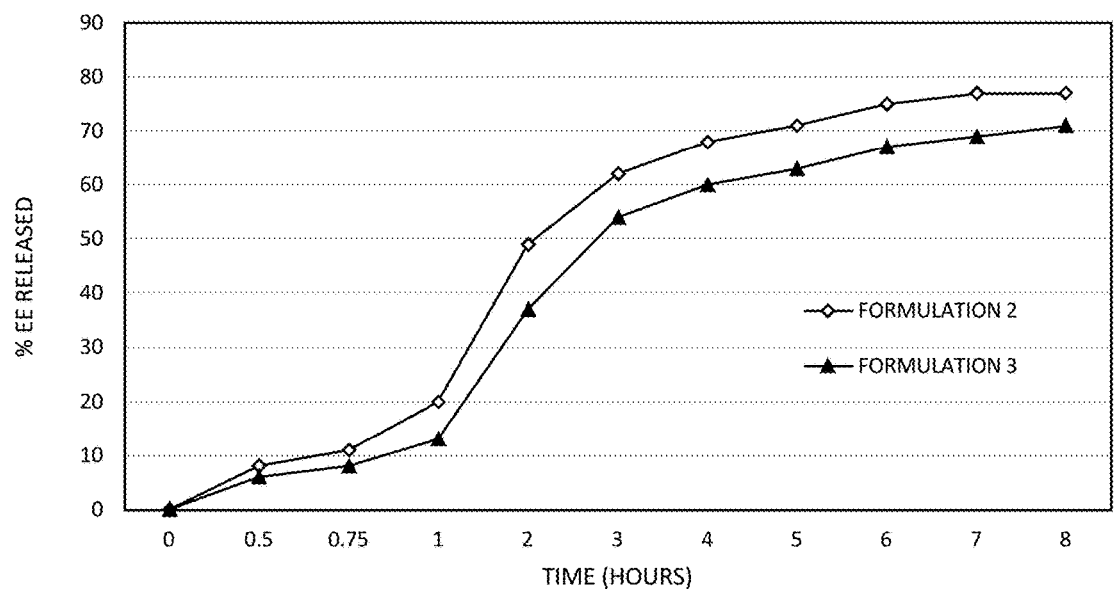
FIG. 8B. EE dissolution profiles of formulations 2 and 3.

The dissolution profile of dienogest and EE in formulations 2 and 3 is shown in FIGS. 8A and 8B, respectively.

3.3. Lactose—HPMC/Formulations 4 and 5

Formulations 4 and 5 show the effect of HPMC K100M at concentrations of about 30% and about 50% in the dissolution profile of both dienogest and ethinyl estradiol. The quantity of HPMC was adjusted by changing the quantity of lactose. Table 9 shows the qualitative and quantitative composition of Formulations 4 and 5.

TABLE 9

| Material | Formulation 4 mg/tablet | % | Formulation 5 mg/tablet | % |
|---|---|---|---|---|
| CORE | | | | |
| Dienogest | 2.00 | 3.75 | 2.00 | 3.75 |
| Ethinyl estradiol | 0.02 | 0.04 | 0.02 | 0.04 |
| Lactose | 29.48 | 55.20 | 19.48 | 36.48 |
| HPMC K100M | 15.00 | 28.10 | 25.00 | 46.82 |
| Povidone K30 | 2.50 | 4.68 | 2.50 | 4.68 |
| Ethanol 96% | * | * | * | * |

TABLE 9-continued

| Material | Formulation 4 mg/tablet | % | Formulation 5 mg/tablet | % |
|---|---|---|---|---|
| Water | * | * | * | * |
| Magnesium stearate | 1.00 | 1.87 | 1.00 | 1.87 |
| COATING | | | | |
| Opadry 2 white | 1.00 | 1.87 | 1.00 | 1.87 |
| PEG 6000 | 2.40 | 4.49 | 2.40 | 4.49 |
| Total | 50.0 | 100 | 50.0 | 100 |

* Evaporated during the process

Manufacturing Process:

HPMC and lactose (1$^{st}$ fraction, 16 mg) were granulated with the binder solution: Water, Ethanol 96%, Povidone K30. The granules obtained were mixed and blended with dienogest, Ethinyl estradiol and the remaining lactose (2$^{nd}$ fraction). The granules were lubricated with Magnesium stearate and compressed to round, biconvex tablets, diameter 5.0 mm, average weight 50.0 mg. Film coating of tablet cores with white Opadry and PEG6000 in film coater HT0003.

Figure 9A:
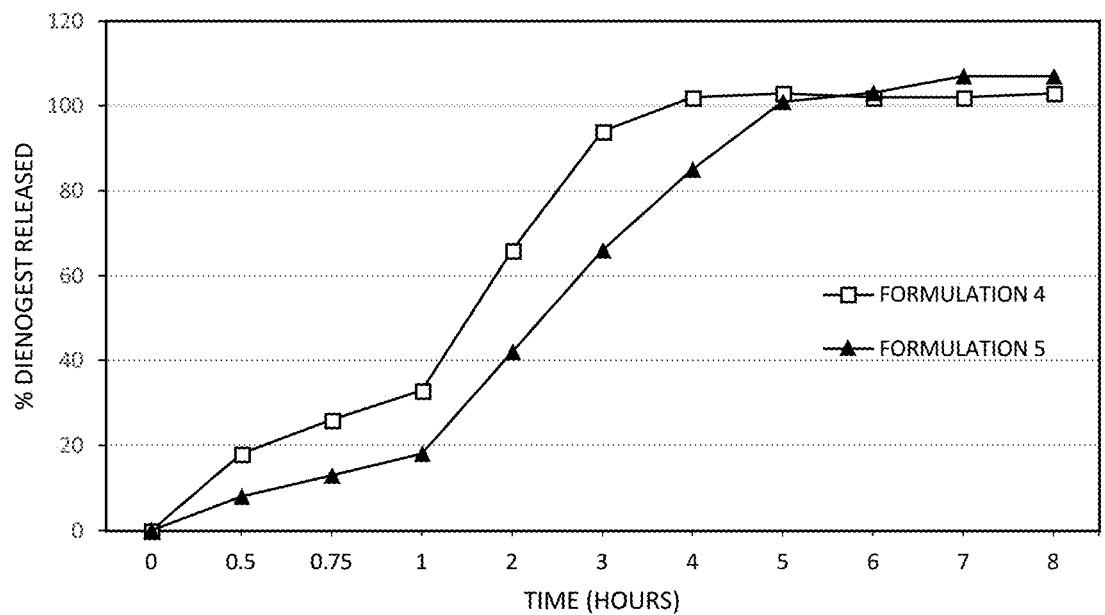
FIG. 9A. DNG dissolution profiles of formulations 4 and 5.
Figure 9B:
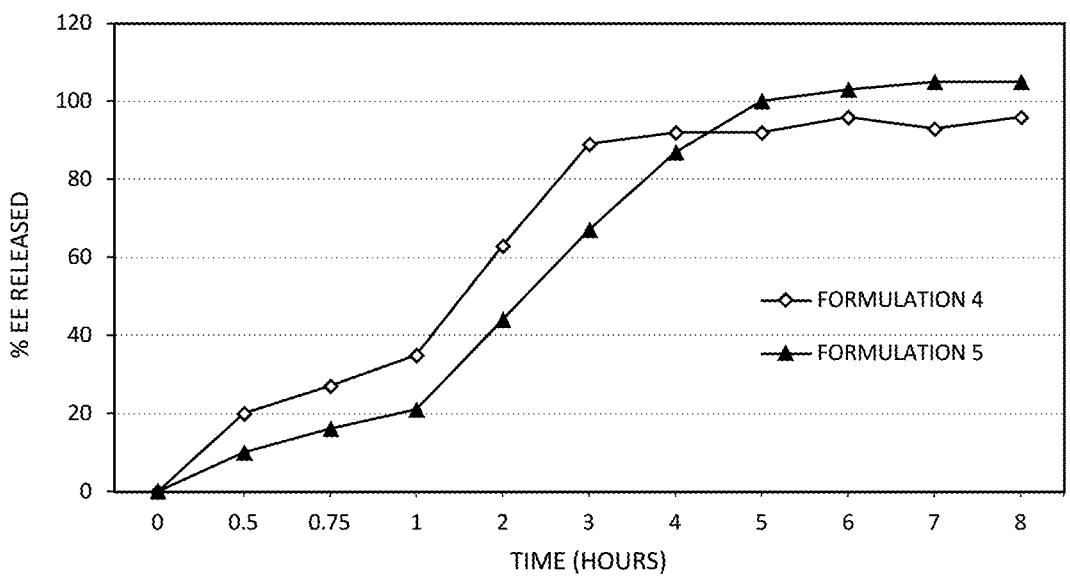
FIG. 9B. EE dissolution profiles of formulations 4 and 5.

The dissolution profile of dienogest and EE in formulations 4 and 5 is shown in FIGS. 9A and 9B, respectively.

Batch with 50% HPMC (i.e., 46.82% of HPMC) presents the preferred prolonged-release profile.

Example 3.2. Dissolution Profile of the Tested Prolonged Release Formulations in Example 2

Table 10 below provides the qualitative and quantitative composition of formulations 6 to 8, comprising 1 mg DNG/0.01 mg EE, 2 mg DNG/0.01 mg EE, and 2 mg DNG/0.02 mg, respectively.

These formulations are lactose-HPMC formulations with about 50% HPMC K100M produced by the same method disclosed under 3.3. above.

TABLE 10

| Material | Formulation 6 mg/tablet | % | Formulation 7 mg/tablet | % | Formulation 8 mg/tablet | % |
|---|---|---|---|---|---|---|
| CORE | | | | | | |
| Dienogest | 1.00 | 1.87 | 2.00 | 3.75 | 2.00 | 3.75 |
| Ethinyl estradiol | 0.01 | 0.02 | 0.01 | 0.02 | 0.02 | 0.04 |
| Lactose monhydrate | 20.49 | 38.37 | 19.48 | 36.50 | 19.48 | 36.48 |
| HPMC K100M | 25.00 | 46.82 | 25.00 | 46.82 | 25.00 | 46.82 |
| Povidone K30 | 2.50 | 4.68 | 2.50 | 4.68 | 2.50 | 4.68 |
| Ethanol 96% | * | * | * | * | * | * |
| Water | * | * | * | * | * | * |
| Magnesium stearate | 1.00 | 1.87 | 1.00 | 1.87 | 1.00 | 1.87 |
| COATING | | | | | | |
| Opadry 2 yelow | 1.00 | 1.87 | — | — | — | — |
| Opadry 2 pink | — | — | 1.00 | 1.87 | — | — |
| Opadry 2 white | — | — | — | — | 1.00 | 1.87 |
| PEG 6000 | 2.40 | 4.49 | 2.40 | 4.49 | 2.40 | 4.49 |
| Total | 53.4 | 100 | 53.4 | 100 | 53.4 | 100 |

Figure 10A:
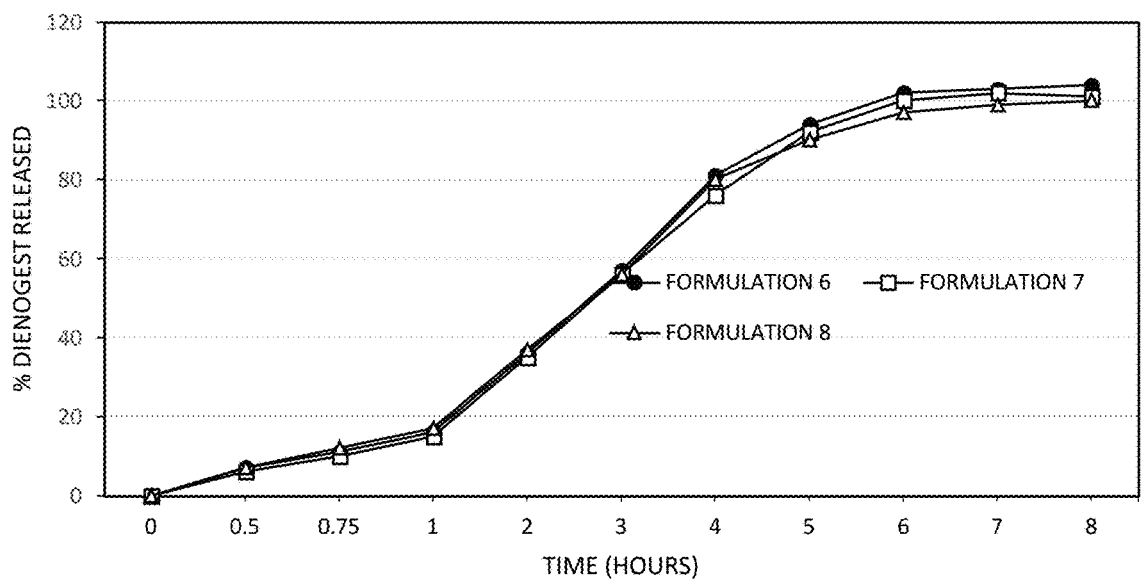
FIG. 10A. DNG dissolution profiles of formulations 6 to 8.
Figure 10B:
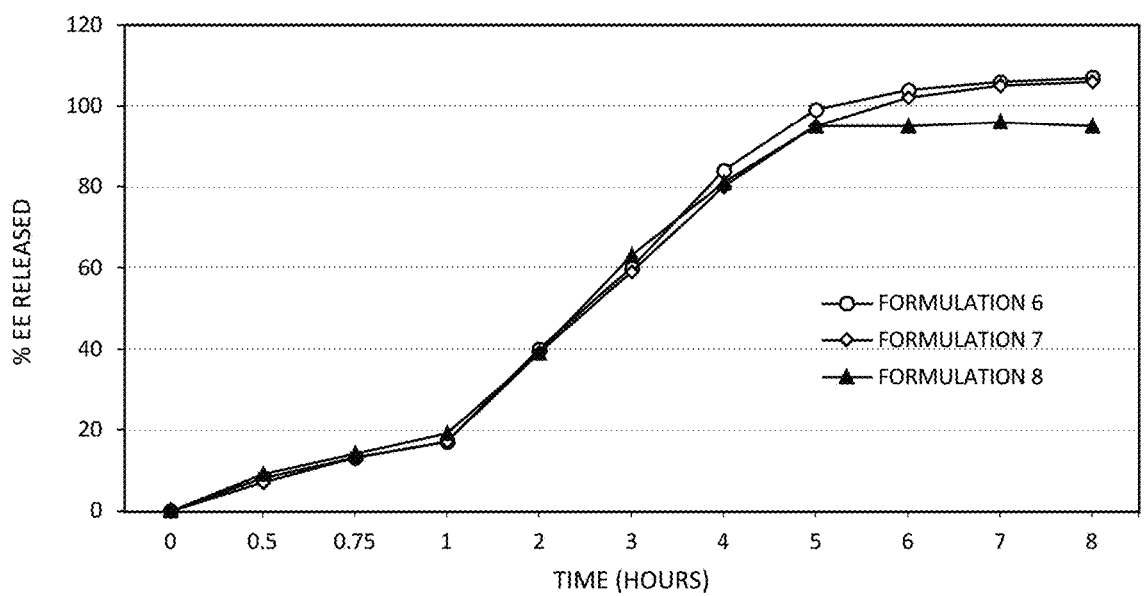
FIG. 10B. EE dissolution profiles of formulations 6 to 8.

The dissolution profile of dienogest and EE in formulations 6 to 8 are shown in FIGS. 10A and 10B, respectively. It can be seen that the various batches produced present almost overlapping dissolution profiles.

REFERENCE LIST

Hoogland H J, Skouby S O. Ultrasound evaluation of ovarian activity under oral contraceptives. Contraception. 1993 June; 47(6):583-90.

Klipping C, Duijkers I, Remmers A, et al. Ovulation-inhibiting effects of dienogest in a randomized, dose-controlled pharmacodynamic trial of healthy women, J Clin Pharmacol. 2012 November; 52(11):1704-13.

Landgren B M, Undén A L, Diczfalusy E. Hormonal profile of the cycle in 68 normally menstruating women. Acta Endocrinol (Copenh). 1980 May; 94(1):89-98.

Nappi R. E., Lete I., Lee L. K., Flores N. M., Micheletti M.-C., Tang B., Real-world experience of women using extended-cycle vs monthly-cycle combined oral contraception in the United States: the National health and Wellness Survey. BMC Women's Health 2018 18:1 Article Number 22.

Wiegratz I, Stahlberg S, Manthey T, et al. Effect of extended-cycle regimen with an oral contraceptive containing 30 mcg ethinyl estradiol and 2 mg dienogest on bleeding patterns, safety, acceptance and contraceptive efficacy. Contraception. 2011 August; 84(2):133-43.

Wiegratz I, Kutschera E, Lee J H, et al. Effect of four different oral contraceptives on various sex hormones and serum-binding globulins. Contraception. 2003; 67(1):25-32.

Wiegratz I, Lee J H, Kutschera E, Winkler U H, Kuhl H. Effect of four oral contraceptives on hemostatic parameters. Contraception. 2004; 70(2):97-106.

Helmerhorst F M, Rosendaal F R, Vandenbroucke J P. Venous thromboembolism and the pill. The WHO technical report on cardiovascular disease and steroid hormone contraception: state-of-the-art. World Health Organization. Hum Reprod. 1998; 13(11): 2981-2983.

Meade T W. Oral contraceptives, clotting factors, and thrombosis. Am J Obstet Gynecol. 1982; 142(6 Pt 2):758-761.

Gerstman B B, Piper J M, Tomita D K, Ferguson W J, Stadel B V, Lundin F E. Oral contraceptive estrogen dose and the risk of deep venous thromboembolic disease. Am J Epidemiol. 1991; 133(1):32-37.

Lidegaard O. Oral contraception and risk of a cerebral thromboembolic attack: results of a case-control study. BMJ. 1993; 306(6883):956-963.

Guida M, Bifulco G, Di Spiezio Sardo A, Scala M, Fernandez L M, Nappi C. Review of the safety, efficacy and patient acceptability of the combined dienogest/estradiol valerate contraceptive pill. *Int J Womens Health.* 2010; 2:279-290.

Stanczyk F Z, Archer D F, Bhavnani B R. Ethinyl estradiol and 17β-estradiol in combined oral contraceptives: pharmacokinetics, pharmacodynamics and risk assessment. *Contraception.* 2013; 87(6):706-727. doi:10.1016/j.contraception.2012.12.011

CLAUSES

1. An oral contraceptive composition comprising 2 mg of 17α-cyanomethyl-17-ß-hydroxyestra-4,9-dien-3-one (dienogest) and 0.02 mg of 17α-ethinylestradiol (ethynyl estradiol), wherein the pharmaceutical form of said contraceptive composition is an extended release form wherein the content of ethynyl estradiol (EE) is intended for slow release.
2. The oral contraceptive composition according to clause 1, wherein the content of dienogest (DNG) and ethynyl estradiol (EE) is intended for slow release.
3. The oral contraceptive composition according to any of clauses 1 or 2, wherein the extended release form is a tablet and comprises a tablet core which comprises the total content of dienogest and ethynyl estradiol within the tablet.
4. The oral contraceptive composition according to any of clauses 1 to 3, wherein the pharmaceutical form is a film-coated tablet comprising a tablet core and a film coating.
5. The oral contraceptive composition according to any of clauses 1 to 4, wherein said composition presents a pharmacokinetic profile further to oral administration under fasting conditions once daily for 7 days characterized by:
   a. a Tmax of EE from 3.5 h to 4 h, preferably around 3.75 h.
6. The oral contraceptive composition according to any of clauses 1 to 5, wherein said composition presents a pharmacokinetic profile further to oral administration under fasting conditions once daily for 7 days characterized by:
   a. a Tmax of DNG from 3.5 h to 4 h, preferably around 3.75 h; and
   b. a Tmax of EE from 3.5 h to 4 h, preferably around 3.75 h.
7. The oral contraceptive composition according to any of clauses 1 to 6, wherein said composition presents a pharmacokinetic profile further to oral administration under fasting conditions once daily for 7 days, further characterized by a Cmax of EE from 60 ng/mL to 65 ng/mL, preferably a Cmax of EE from 60 ng/mL to 65 ng/mL and a Cmax of DNG from 55 ng/mL to 60 ng/mL.
8. The oral contraceptive composition according to any of clauses 1 to 7, wherein said composition presents a pharmacokinetic profile further to oral administration under fasting conditions once daily for 7 days, further characterized by having an AUC(0-τ) for EE from 680 to 710 ng*h/mL, preferably an AUC(0-τ) for EE from 680 to 710 ng*h/mL and an AUC(0-τ) for DNG from 710 to 740 ng*h/mL.
9. The contraceptive composition according to any of clauses 1 to 8, wherein when the composition is subjected to an in vitro dissolution test according to USP1 (baskets) method, EE, preferably DNG and EE, respectively, has a dissolution profile characterized in that:
   (i) no more than 25% of the amount initially present in said composition is dissolved within 1 hour; and
   (ii) between 30% and 60% of the amount initially present in said composition is dissolved within 2 hours,
   (iii) at least 70%, of the amount initially present in said composition is dissolved within 8 hours.
10. The contraceptive composition according to clause 9, wherein EE, preferably DNG and EE, respectively, has a dissolution profile characterized in that:
    (i) no more than 25% of the amount initially present in said composition is dissolved within 1 hour;
    (ii) between 35% and 55% of the amount initially present in said composition is dissolved within 2 hours, and
    (iii) at least 80% of the amount initially present in said composition is dissolved within 5 hours.
11. The contraceptive composition according to any of clauses 1 to 10, wherein said composition is suitable for administration as the daily active oral form in a contraceptive regimen comprising the administration of the active oral form daily for 21 to 24 consecutive days followed by a period of 4 to 7 days of daily administration of a placebo oral form or no oral form administration.
12. The contraceptive composition according to clause 11, wherein said composition is suitable for administration as the daily active oral form in a contraceptive regimen comprising the administration of the active oral form for 24 consecutive days followed by a period of 4 days of daily administration of a placebo oral form.

13. The contraceptive composition according to any of clauses 1 to 10, wherein said composition is suitable for administration as the daily active oral form in a contraceptive regimen comprising the administration of the active oral form daily for 87 consecutive days followed by a period of 4 days of daily administration of a placebo oral form or no oral form administration.

14. The contraceptive composition according to any of clauses 1 to 13, wherein EE, preferably EE and DNG, are dispersed in a sustained-release matrix.

15. The contraceptive composition according to any of clauses 1 to 14, wherein said sustained-release matrix comprises a hydrophilic polymer, preferably said matrix is obtained by granulation of EE, preferably DNG and EE, with said hydrophilic polymer.

16. The contraceptive composition according to clause 15, wherein said hydrophilic polymer is a cellulosic derivative, preferably a hydroxyalkyl cellulose, at a range from 25% to 60% w/w, preferably from 30% to 50% w/w, more preferably from 45% to 55% w/w, even more preferably around 50% w/w.

17. The contraceptive composition according to any of clauses 15 or 16, wherein said hydrophilic polymer is selected from hydroxyethyl cellulose, hydroxypropyl cellulose, hydroxypropyl methylcellulose (HPMC) and a combination thereof, preferably said hydrophilic polymer is HMPC, more preferably HPMC K100.

18. The contraceptive composition according to any of clauses 1 to 17, wherein said composition comprises:
a diluent, preferably at 30-60% w/w;
a polymeric matrix forming agent, preferably at 10-60% w/w;
a binder, preferably at 1-10% w/w; and
a lubricant, preferably at 0-5% w/w.

19. The contraceptive composition according to any of clauses 1 to 18, wherein said composition comprises:
lactose at 35-45% w/w;
HPMC at 45-55% w/w;
povidone at 2-7% w/w; and
magnesium stearate at 1-3% w/w.

20. The contraceptive composition according to any of clauses 1 to 19, wherein said composition comprises or consists of:
lactose monohydrate around 40% w/w;
HPMC K100 low viscosity around 50% w/w;
povidone K30 around 5% w/w; and
magnesium stearate around 2% w/w.

21. A process for obtaining a contraceptive composition as described in any of clauses 1 to 20, wherein said method comprises:
i. independently mixing each of DNG and EE with a diluent, and then mixing these together to obtain a mixture of DNG, EE and said diluent;
ii. granulating a diluent and a polymeric matrix forming agent;
iii. drying, optionally sieving, and mixing the granules obtained in step ii) with the mixture obtained in step i);
iv. blending the mixture obtained in step iii) with a lubricant, and then compress into tablets;
v. optionally coating the tablets obtained in step iv) with a coating agent and dry.

22. A contraceptive kit comprising one or more packaging units wherein each packaging unit comprises at least 21 to 24 oral contraceptive compositions according to any of clauses 1 to 12 or 14-20 as daily active dosage forms and at least 4 to 7 daily placebo dosage forms.

The invention claimed is:
1. An oral contraceptive composition, in the form of a tablet, wherein the tablet comprises:
(a) 2 mg of 17α-cyanomethyl-17-ß-hydroxyestra-4,9-dien-3-one (dienogest, DNG);
(b) 0.02 mg of 17α-ethinylestradiol (ethynyl estradiol, EE); and,
(c) 20% to 60% w/w of a polymeric matrix forming agent based on a total weight of the composition,
wherein:
the 0.02 mg of EE is formulated with a controlled release material comprising the polymeric matrix forming agent, such that all of the EE in the contraceptive composition is subject to extended release;
the DNG and the EE are formulated such that, when the composition is subjected to an in vitro dissolution test according to USP1 (baskets) method using 900 mL of water at 37° C. (=0.5° C.) at a stirring rate of 75 rpm, the DNG and the EE, respectively, exhibit a dissolution profile such that:
no more than 20% of the EE initially present in the composition is dissolved within 0.5 hour, and
between 30% and 60% of the DNG initially present in the composition, and between 30% and 60% of the EE initially present in the composition, is dissolved within 2 hours; and
the extended release of the DNG and the EE occur at rates that are independent of pH.

2. The contraceptive composition of claim 1, wherein after once daily oral administration to a human premenopausal female under fasting conditions for 7 days, the oral contraceptive composition provides:
a Cmax of EE ranging from 60 pg/mL to 65 pg/mL; and
a Cmax of DNG ranging from 55 ng/mL to 60 ng/mL.

3. The contraceptive composition of claim 1, wherein after once daily oral administration to a human premenopausal female under fasting conditions for 7 days, the oral contraceptive composition provides:
a Tmax of EE ranging from 3.5 hours to 4.0 hours; and
a Tmax of DNG ranging from 3.5 hours to 4.0 hours.

4. The contraceptive composition of claim 1, wherein after once daily oral administration to a human premenopausal female under fasting conditions for 7 days, the oral contraceptive composition provides:
an $AUC_{0-24hr}$ of EE ranging from 680 pgxh/mL to 710 pgxh/mL; and
an $AUC_{0-24hr}$ of DNG ranging from 710 ngxh/mL to 740 ngxh/mL.

5. The contraceptive composition of claim 1, wherein after once daily oral administration to a human premenopausal female under fasting conditions for 7 days, the oral contraceptive composition provides:
a Cmax of EE ranging from 60 μg/mL to 65 μg/mL;
a Tmax of EE ranging from 3.5 hours to 4.0 hours;
an $AUC_{0-24hr}$ of EE ranging from 680 pgxh/mL to 710 pgxh/mL;
a Cmax of DNG ranging from 55 ng/ml to 60 ng/mL;
a Tmax of DNG ranging from 3.5 hours to 4.0 hours; and
an $AUC_{0-24hr}$ of DNG ranging from 710 ngxh/mL to 740 ngxh/mL.

6. The contraceptive composition according to claim 1, wherein when the composition is subjected to an in vitro dissolution test according to USP1 (baskets) method using 900 mL of water at 37° C. (±0.5° C.) at a stirring rate of 75 rpm, the DNG and the EE, respectively, exhibit a dissolution profile such that no more than 20% of the DNG initially present in the composition, and no more than 20% of the EE initially present in the composition, is dissolved within 0.5 hour.

7. The oral contraceptive composition of claim 1, wherein the tablet comprises 30-60% w/w of the polymeric matrix forming agent.

8. The oral contraceptive composition of claim 1, wherein the tablet further comprises:
30-60% w/w of a diluent;
1-10% w/w of a binder; and
0-5% w/w of a lubricant.

9. The oral contraceptive composition of claim 7, wherein the tablet comprises:
2 mg of the DNG;
0.02 mg of the EE;
35-45% w/w of a lactose based on the total weight of the composition;
45-55% w/w of a hydroxypropyl methylcellulose (HPMC) based on a total weight of the composition;
2-7% w/w of a povidone based on the total weight of the composition; and
1-3% w/w of a stearate based on the total weight of the composition.

10. The contraceptive composition according to claim 1, wherein when the composition is subjected to an in vitro dissolution test according to USP1 (baskets) method using 900 mL of water at 37° C. (±0.5° C.) at a stirring rate of 75 rpm, the DNG and the EE, respectively, exhibit a dissolution profile wherein at least 70% of the DNG and at least 70% of the EE initially present in the composition is dissolved within 8 hours.

11. The contraceptive composition according to claim 1, wherein when the composition is subjected to an in vitro dissolution test according to USP1 (baskets) method using 900 mL of water at 37° C. (±0.5° C.) at a stirring rate of 75 rpm, the DNG and the EE, respectively, exhibit a dissolution profile wherein:
(i) no more than 25% of the DNG and no more than 25% of the EE initially present in the composition is dissolved within 1 hour;
(ii) between 30% and 60% of the DNG and between 30% and 60% of the EE initially present in the composition is dissolved within 2 hours; and
(iii) at least 70% of the DNG and at least 70% of the EE initially present in the composition is dissolved within 8 hours.

12. The contraceptive composition according to claim 1, wherein when the composition is subjected to an in vitro dissolution test according to USP1 (baskets) method using 900 mL of water at 37° C. (±0.5° C.) at a stirring rate of 75 rpm, the DNG and the EE, respectively, exhibit a dissolution profile wherein:
(i) no more than 25% of the DNG and no more than 25% of the EE initially present in the composition is dissolved within 1 hour;
(ii) between 30% and 55% of the DNG and between 30% and 55% of the EE initially present in the composition is dissolved within 2 hours; and
(iii) at least 80% of the DNG and at least 80% of the EE initially present in the composition is dissolved within 5 hours.

13. The contraceptive composition according to claim 1, wherein, after once daily oral administration to human premenopausal female under fasting conditions for 7 days, the oral contraceptive composition provides:
a Cmax of EE of about 63.6 pg/mL;
a Tmax of EE of about 3.75 hours;
an $AUC_{0-24\,hr}$ of EE of about 706.3 pgxh/mL;
a Cmax of DNG of about 59.3 ng/ml;
a Tmax of DNG of about 3.75 hours; and
an $AUC_{0-24\,hr}$ of DNG of about 731.6 ngxh/mL.

14. The contraceptive composition according to claim 1, wherein the composition is formulated for administration as a daily active oral form in a contraceptive regimen comprising administration of the daily active oral form for 21 to 24 consecutive days followed by a period of 4 to 7 days of daily administration of a placebo oral form or no oral form administration.

15. The contraceptive composition according to claim 14, wherein the contraceptive regimen comprises administration of the daily active oral form for 24 consecutive days followed by a period of 4 days of daily administration of a placebo oral form.

16. The contraceptive composition according to claim 1, wherein the tablet is a film-coated tablet.

17. The contraceptive composition according to claim 16, wherein the film coating of the film-coated tablet comprises a polymer, a plasticizer and a pigment.

18. The contraceptive composition according to claim 17, wherein the polymer comprises a polyethylene glycol.

19. The contraceptive composition according to claim 17, wherein the polymer comprises a polyethylene glycol having an average molecular weight within 5,000-7,000 Daltons.

20. A contraceptive kit, comprising one or more packaging units wherein each packaging unit comprises at least 21 to 24 oral contraceptive compositions according to claim 1 as daily active dosage forms and at least 4 to 7 daily placebo dosage forms.

21. The contraceptive kit of claim 20, wherein each packaging unit comprises 24 of the oral contraceptive compositions as daily active dosage forms and 4 of the daily placebo dosage forms.

22. A method for oral contraception in a female subject in need thereof, the method comprising:
(i) a first phase wherein active daily dosage units of the oral contraceptive composition of claim 1 are administered to the female subject over a period of 21 to 27 consecutive days; and
(ii) a second phase wherein no contraceptive composition is administered to the female subject over a period of 1 to 7 consecutive days.

23. The method of claim 22, wherein the first phase lasts from 21 to 24 consecutive days, and the second phase lasts from 4 to 7 consecutive days.

24. The method of claim 22, wherein the first phase lasts 24 consecutive days, and the second phase lasts 4 consecutive days.

* * * * *

UNITED STATES PATENT AND TRADEMARK OFFICE
CERTIFICATE OF CORRECTION

| | | |
|---|---|---|
| PATENT NO. | : 12,409,142 B2 | Page 1 of 1 |
| APPLICATION NO. | : 18/660021 | |
| DATED | : September 9, 2025 | |
| INVENTOR(S) | : Enrico Colli | |

It is certified that error appears in the above-identified patent and that said Letters Patent is hereby corrected as shown below:

In the Claims

Column 34, Claim 1, Line 18:
"(=0.5° C.)" should read: -- (±0.5° C.) --.

Column 34, Claim 5, Line 54:
"60 µg/mL to 65 µg/mL;" should read: -- 60 pg/mL to 65 pg/mL; --.

Signed and Sealed this
Ninth Day of December, 2025

John A. Squires
*Director of the United States Patent and Trademark Office*